US012122808B2

(12) United States Patent
Reynolds

(10) Patent No.: US 12,122,808 B2
(45) Date of Patent: Oct. 22, 2024

(54) **CONTROL OF *SPODOPTERA***

(71) Applicant: SYNGENTA CROP PROTECTION AG, Basel (CH)

(72) Inventor: Clarence Michael Reynolds, Research Triangle Park, NC (US)

(73) Assignee: SYNGENTA CROP PROTECTION AG, Basel (CH)

( * ) Notice: Subject to any disclaimer, the term of this patent is extended or adjusted under 35 U.S.C. 154(b) by 27 days.

(21) Appl. No.: 17/616,276

(22) PCT Filed: Jun. 3, 2020

(86) PCT No.: PCT/US2020/035876

§ 371 (c)(1),
(2) Date: Dec. 3, 2021

(87) PCT Pub. No.: WO2020/247465

PCT Pub. Date: Dec. 10, 2020

(65) Prior Publication Data

US 2022/0324920 A1 Oct. 13, 2022

Related U.S. Application Data

(60) Provisional application No. 62/857,504, filed on Jun. 5, 2019.

(51) Int. Cl.
*C07K 14/195* (2006.01)
*A01N 63/50* (2020.01)
*C12N 15/82* (2006.01)

(52) U.S. Cl.
CPC ............ *C07K 14/195* (2013.01); *A01N 63/50* (2020.01); *C12N 15/8286* (2013.01)

(58) Field of Classification Search
None
See application file for complete search history.

(56) References Cited

U.S. PATENT DOCUMENTS

| | | | | |
|---|---|---|---|---|
| 7,285,632 | B2 | 10/2007 | Apel-Birkhold et al. | |
| 9,347,072 | B2 | 5/2016 | Warren et al. | |
| 2004/0055036 | A1 † | 3/2004 | East | |
| 2006/0094013 | A1 | 5/2006 | Takemori | |
| 2017/0058294 | A1 * | 3/2017 | Bowen | A01N 63/50 |
| 2017/0193683 | A1 | 7/2017 | Wong et al. | |
| 2022/0089658 | A1 | 3/2022 | Sessler et al. | |
| 2022/0324920 | A1 | 10/2022 | Reynolds et al. | |

FOREIGN PATENT DOCUMENTS

| | | | |
|---|---|---|---|
| CN | 113302199 | A | 8/2021 |
| JP | 2006-500908 | A | 1/2006 |
| JP | 2022-536083 | A | 8/2022 |
| WO | 9903328 | A1 | 1/1999 |
| WO | 2004/018669 | A1 | 3/2004 |
| WO | 2017005819 | A1 | 1/2017 |
| WO | 2017087026 | A1 | 5/2017 |

OTHER PUBLICATIONS

Zhan et al, Cloning, Expression and Prediction of Txp40 Toxic Protein Gene of *Photobacteria* (NLK-1), 2018 Microbiology China 20: 1262-1272) (Year: 2018).*
Brown et al, Txp40, a Ubiquitous Insecticidal Toxin Protein from *Xenorhabdus* and *Photorhabdus* Bacteria, 2006, Applied and Environmental Microbiology 72: 1653-1662 (Year: 2006).*
NCBI accession KY814642, 2018, https://www.ncbi.nlm.nih.gov/nuccore/KY814642.1 (Year: 2018).*
NCBI accession DQ242625, 2006, https://www.ncbi.nlm.nih.gov/protein/78173141 (Year: 2006).*
Rodou et al, 2010, Toxins and Secretion Systems of *Photorhabdus luminescens* Toxins 2: 1250-1264 (Year: 2010).*
Gulzar, Effects of entomopathogenic nematodes *Steinernema carpocapsae* and *Heterorhabditis bacteriophora* on the fitness of a Vip3A resistant subpopulation of *Heliothis virescens* (Noctuidae: Lepidoptera) 2020, Bragantia 79:281-292 (Year: 2020).*
Written Opinion of the International Searching Authority and International Search Report cited in International Application No. PCT/US2020/035876, mailed Dec. 14, 2020.
Brown et al., "Txp40, a Ubiqutous Insecticidal toxin Protein from *Xenorhabdus* and *Photorhabdus* Bacteria," Applied and Enviormental Michrobiology, Feb. 3, 2006, vol. 72., Issue 2, pp. 1653-1662.
Supplementary European Search Report issued in European Application No. EP 20818642.9 dated May 11, 2023.
Mathur, et al., "A 37 kDa Txp40 protein characterized from *Photorhabdus luminescens* sub sp. *akhurstii* conferred injectable and oral toxicity to greater wax moth, *Galleria mellonella*", Toxicon, vol. 154, pp. 69-73, 2018.
Brown et al., Txp40, a Ubiquitous Insecticidal Toxin Protein from *Xenorhabdus* and *Photorhabdus* Bacteria, Applied and Environmental Microbiology, Feb. 2006, p. 1653-1662 and Supplemental Material Figure 1.†
Shankhu et al., Txp40, a protein from *Photorhabdus akhurstii*, conferred potent insecticidal activity against the larvae of *Helicoverpa armigera, Spodoptera litura* and *S. exigua*, Pest Manag Sci 2020 (accepted article published Dec. 22, 2019); 76: pp. 2004-2014.†

(Continued)

*Primary Examiner* — Anne Kubelik
*Assistant Examiner* — Aleksandar Radosavljevic
(74) *Attorney, Agent, or Firm* — BakerHostetler; Toni-Junell Herbert

(57) ABSTRACT

Methods for controlling plant pests are disclosed. In particular, insecticidal proteins having toxicity to *Spodoptera* insect pests are provided. Polynucleotides comprising codons optimized for expression in plants encoding the insecticidal proteins are also provided. Methods of making the insecticidal proteins and methods of using the insecticidal proteins and polynucleotides encoding the insecticidal proteins of the invention, for example in transgenic plants to confer protection from insect damage, are also disclosed.

17 Claims, No Drawings

Specification includes a Sequence Listing.

(56) References Cited

OTHER PUBLICATIONS

Mathur et al., A 37 kDa Txp40 protein characterized from *Photorhabdus luminescens* sub sp. *akhurstii* conferred injectable and oral toxicity to greater wax moth, *Galleria mellonella*, Toxicon 154 (2018), pp. 69-73.†
Alamalakala et al., Chapter 5: Non-Bt Soil Microbe-Derived Insecticidal Proteins, Biocontrol of Lepidopteran Pests, Soil Biology 43, 2015, pp. 89-121 (351 pages total).†
Malone et al., Chapter 13: Beyond Bt: Alternative Strategies for Insect-Resistant Genetically Modified Crops, Integration of Insect-Resistant Genetically Modified Crops within IPM Programs, 2008, pp. 357-417.†
Sena et al., Interaction of Bacillus thuringiensis Cry1 and Vip3A Proteins with *Spodoptera frugiperda* Midgut Binding Sites, Applied and Environmental Microbiology, Apr. 2009, pp. 2236-2237.†
Zhan, Database GenBank [online], Accession No. AVJ54817.1, Mar. 10, 2018, 1 page, published at https://www.ncbi.nlm.nih.gov/protein/avj54817.1.†
Zhan, Database GenBank [online], Accession No. KY814642.1, Mar. 10, 2018, 2 pages, published at https://www.ncbi.nlm.nih.gov/nuccore/ky814642.1.†
Dutta et al., Database GenBank [online], Accession No. AWM11673.1, May 27, 2018, 1 page, published at https://www.ncbi.nlm.nih.gov/protein/awm11673.1.†

* cited by examiner
† cited by third party

CONTROL OF *SPODOPTERA*

CROSS-REFERENCE TO RELATED APPLICATIONS

This application is a 371 National Stage application of International Application No. PCT/US2020/035876 filed Jun. 3, 2020, which claims priority to U.S. 62/857,504, filed Jun. 5, 2019, the entire contents of these applications are hereby incorporated by reference.

SEQUENCE LISTING

A Sequence Listing in ASCII text format, submitted under 37 C.F.R. § 1.821, entitled "81889-WO-REG-ORG-P-1_ST25.txt", 308 kilobytes in size, generated on May 31, 2020 and filed via EFS-Web is provided in lieu of a paper copy. This Sequence Listing is hereby incorporated by reference into the specification for its disclosures.

FIELD OF THE INVENTION

The present invention relates to the fields of pest insect control, protein engineering and plant molecular biology. More particularly the invention relates to methods of controlling pest insects in the order Spodoptera, particularly *Spodoptera frugiperda* (fall armyworm; FAW), using a txp40 gene or Txp40 protein or using a Txp40 protein in combination with a second pest control agent. The invention also relates to methods of protecting crops, particularly corn, against *Spodoptera*, particularly FAW, and more particularly against a Cry- and/or Vip3-resistant FAW. The present invention also provides a Txp40 protein toxin and its variants having insecticidal activity against FAW, nucleic acids whose expression results in the insecticidal proteins, and methods of making and methods of using the insecticidal proteins and corresponding nucleic acids to control FAW pests. This invention also relates to a plant, especially a monocot, particularly a corn plant, infestable by FAW and transformed with an expressible txp40 gene or with both an expressible txp40 gene and a gene encoding a second pesticidal agent.

BACKGROUND

*Spodoptera* species, including *Spodoptera frugiperda* (fall armyworm, FAW), are serious pests of several row crops, including corn, cotton and soybean. FAW is the most destructive consistent pest species of corn plants (*Zea mays*; maize) in Brazil and other South American countries, causing up to a 57% reduction in yield. In certain years, FAW can also cause significant economic damage to corn in other countries including the US. The larvae of this insect initially feed on leaf tissue before entering deep in the whorl where significant damage to the developing tassel occurs. Defoliation caused by FAW reduces photosynthetic area, which may stunt plants and reduce yield. FAW larvae also damage ears by boring through the side of ear and feeding on developing kernels reducing grain quality and yield.

Historically, the control of FAW in corn has been accomplished using synthetic insecticides. However, such insecticides are only effective on young larvae and before they burrow deep into the whorl or the ear. In addition, in regions of intensive corn cultivation, FAW populations have evolved resistance to several insecticides, such as lambda-cyhalothrin, chlorpyrifos, spinosad and lufenuron.

Other FAW control options have more recently included the use of transgenic corn plants expressing one or more insecticidal crystal proteins (Cry proteins) and/or vegetative insecticidal proteins (VIPs) derived from the bacterium *Bacillus thuringiensis* (Bt). The most potent FAW-active protein from Bt to date is the vegetative insecticidal protein, Vip3. Only a very few Cry proteins from Bt are active against FAW. Those few that have moderate to high activity include Cry1Ab, Cry1Be, Cry1D, Cry1F, Cry1If, Cry1J and Cry2A. Since about 2007, the commercial release of transgenic corn events expressing one or more of these Cry proteins and the Vip3 protein has provided a new tactic for FAW management. Currently, products containing these so called Bt events are cultivated on much of the major corn-growing areas where FAW is a pest. For example, such products are cultivated on more than 80 of the corn-growing areas in Brazil (~12.5 million ha/year). The rapid adoption of products containing Bt insecticidal proteins with activity against FAW has contributed to a reduction in insecticidal sprays against FAW. However, in some situations, the continuous expression of Bt-derived proteins in corn plants imposes an intense selection pressure on target FAW pest populations, favoring the evolution of resistance. In Brazil, for example, field populations of FAW have evolved resistance to the Cry1F and Cry1Ab proteins expressed in transgenic corn products. FAW has also developed resistance to Cry1F corn in Puerto Rico and in areas of the US. In Brazil, a high frequency of resistance to products with stacked products containing Cry1 proteins has also been reported in populations of FAW. In contrast, no resistance has been detected for the Vip3A protein.

There remains an ongoing need to identify new and effective methods for controlling insect pests of row crops using insecticidal agents that provide an economic benefit to farmers and that are environmentally acceptable. Particularly needed are methods to control *Spodoptera* species, particularly FAW, using proteins that have a different mode of action than existing insecticidal proteins from Bt, such as Cry proteins and/or Vip3 proteins, as a way to mitigate the development of resistance. Furthermore, delivery of insect control agents through products that minimize the burden on the environment, as through transgenic plants, are most desirable.

SUMMARY

In view of these needs, the present invention provides methods of controlling *Spodoptera frugiperda* (fall armyworm; FAW) and other insect pests, using a Txp40 insecticidal protein and variants of a Txp40 insecticidal protein. The invention also provides *Spodoptera*-active Txp40 proteins and variant Txp40 proteins which are substantially identical to Txp40. The proteins of the invention surprisingly have oral toxicity to FAW, an insect pest species that is recalcitrant to many types of insecticidal proteins, particularly to the Cry proteins from Bt. The invention is further drawn to recombinant codon-optimized polynucleotides that encode a Txp40 protein or a variant Txp40 protein.

Also included in the invention are expression cassettes and vectors containing recombinant polynucleotides of the invention; a plant or microorganism which includes and enables expression of such polynucleotides; plants transformed with such polynucleotides, for example transgenic corn plants; the progeny of such plants which contain the polynucleotides stably incorporated and hereditable in a Mendelian manner, and/or the seeds of such plants and such progeny. The invention also includes methods of breeding to introduce a transgene comprising a polynucleotide of the invention into a progeny plant and into various corn germplasms.

The invention also includes compositions and formulations containing Txp40 or its variants, which are capable of inhibiting the ability of FAW to survive, grow and/or reproduce, or of limiting FAW-related damage or loss to crop plants, for example applying Txp40 or its variants as part of compositions or formulations to FAW-infested areas or plants, or to prophylactically treat FAW-susceptible areas or plants to confer protection against the FAW pests.

The invention is further drawn to a method of making Txp40 or its variants and to methods of using the polynucleotides of the invention, for example in microorganisms to control FAW or in transgenic plants to confer protection from FAW damage.

Other aspects and advantages of the invention will become apparent to those skilled in the art from a study of the following description of the invention and non-limiting examples.

BRIEF DESCRIPTION OF THE SEQUENCES IN THE SEQUENCE LISTING

The nucleotide sequences listed in the accompanying sequence listing are shown using standard letter abbreviations for nucleotide bases, as defined in 37 C.F.R. § 1.822. The nucleotide and amino acid sequences listed define molecules (i.e., polynucleotides and polypeptides, respectively) having the nucleotide and amino acid monomers arranged in the manner described. The nucleotide and amino acid sequences listed also each define a genus of polynucleotides or polypeptides that comprise the nucleotide and amino acid monomers arranged in the manner described. In view of the redundancy of the genetic code, it will be understood that a nucleotide sequence including a coding sequence also describes the genus of polynucleotides encoding the same polypeptide as a polynucleotide consisting of the reference sequence. It will further be understood that an amino acid sequence describes the genus of polynucleotide ORFs encoding that polypeptide.

Only one strand of each nucleic acid sequence is shown, but the complementary strand is understood as included by any reference to the displayed strand. As the complement and reverse complement of a primary nucleotide sequence are necessarily disclosed by the primary sequence, the complementary sequence and reverse complementary sequence reference to the nucleotide sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of the nucleotide base uracil (U) for thymine (T)), an RNA sequence is included by any reference to the DNA sequence encoding it. In the accompanying sequence listing:

SEQ ID NO: 1 is a Txp40-1 amino acid sequence from *Phtorhabdus luminescens.*

SEQ ID NO:2 is a variant Txp40-1 amino acid sequence.

SEQ ID NO:3 is a native txp40-1 nucleotide sequence from *Phtorhabdus luminescens.*

SEQ ID NO:4 is an *E. coli* codon-optimized txp40-1 nucleotide sequence.

SEQ ID NO:5 is a maize codon-optimized txp40-1 nucleotide sequence.

SEQ ID NO:6 is a H1Txp40 amino acid sequence from *Photorhabdus* sp.

SEQ ID NO:7 is a H2Txp40 amino acid sequence from *Photorhabdus* sp.

SEQ ID NO:8 is a H3Txp40 amino acid sequence from *Photorhabdus* sp.

SEQ ID NO:9 is a H5Txp40 amino acid sequence from *Photorhabdus* sp.

SEQ ID NO:10 is a Txp40 amino acid sequence from *Xenorhabdus nematophila.*

SEQ ID NO:11 is an *E. coli* codon-optimized txp40-1 K31A variant nucleotide sequence.

SEQ ID NO:12 is an *E. coli* codon-optimized txp40-1 K48A variant nucleotide sequence.

SEQ ID NO:13 is an *E. coli* codon-optimized txp40-1 K49A variant nucleotide sequence.

SEQ ID NO:14 is an *E. coli* codon-optimized txp40-1 K73A variant nucleotide sequence.

SEQ ID NO:15 is an *E. coli* codon-optimized txp40-1 K75A variant nucleotide sequence.

SEQ ID NO:16 is an *E. coli* codon-optimized txp40-1 K103A variant nucleotide sequence.

SEQ ID NO:17 is an *E. coli* codon-optimized txp40-1 K111A variant nucleotide sequence.

SEQ ID NO:18 is an *E. coli* codon-optimized txp40-1 K119A variant nucleotide sequence.

SEQ ID NO:19 is an *E. coli* codon-optimized txp40-1 K133A variant nucleotide sequence.

SEQ ID NO:20 is an *E. coli* codon-optimized txp40-1 K143A variant nucleotide sequence.

SEQ ID NO:21 is an *E. coli* codon-optimized txp40-1 K170A variant nucleotide sequence.

SEQ ID NO:22 is an *E. coli* codon-optimized txp40-1 K191A variant nucleotide sequence.

SEQ ID NO:23 is an *E. coli* codon-optimized txp40-1 K200A variant nucleotide sequence.

SEQ ID NO:24 is an *E. coli* codon-optimized txp40-1 K209A variant nucleotide sequence.

SEQ ID NO:25 is an *E. coli* codon-optimized txp40-1 K210A variant nucleotide sequence.

SEQ ID NO:26 is an *E. coli* codon-optimized txp40-1 K213A variant nucleotide sequence.

SEQ ID NO:27 is an *E. coli* codon-optimized txp40-1 K221A variant nucleotide sequence.

SEQ ID NO:28 is an *E. coli* codon-optimized txp40-1 K238A variant nucleotide sequence.

SEQ ID NO:29 is an *E. coli* codon-optimized txp40-1 K247A variant nucleotide sequence.

SEQ ID NO:30 is an *E. coli* codon-optimized txp40-1 K250A variant nucleotide sequence.

SEQ ID NO:31 is an *E. coli* codon-optimized txp40-1 K263A variant nucleotide sequence.

SEQ ID NO:32 is an *E. coli* codon-optimized txp40-1 K265A variant nucleotide sequence.

SEQ ID NO:33 is an *E. coli* codon-optimized txp40-1 K271A variant nucleotide sequence.

SEQ ID NO:34 is an *E. coli* codon-optimized txp40-1 K275A variant nucleotide sequence.

SEQ ID NO:35 is an *E. coli* codon-optimized txp40-1 K284A variant nucleotide sequence.

SEQ ID NO:36 is an *E. coli* codon-optimized txp40-1 K296A variant nucleotide sequence.

SEQ ID NO:37 is an *E. coli* codon-optimized txp40-1 K309A variant nucleotide sequence.

SEQ ID NO:38 is an *E. coli* codon-optimized txp40-1 K333A variant nucleotide sequence.

SEQ ID NO:39 is an *E. coli* codon-optimized txp40-1 R10A variant nucleotide sequence.

SEQ ID NO:40 is an *E. coli* codon-optimized txp40-1 R26A variant nucleotide sequence.

SEQ ID NO:41 is an *E. coli* codon-optimized txp40-1 R46A variant nucleotide sequence.

SEQ ID NO:42 is an *E. coli* codon-optimized txp40-1 R167A variant nucleotide sequence.

SEQ ID NO:43 is an *E. coli* codon-optimized txp40-1 R186A variant nucleotide sequence.

SEQ ID NO:44 is an *E. coli* codon-optimized txp40-1 R187A variant nucleotide sequence.

SEQ ID NO:45 is an *E. coli* codon-optimized txp40-1 R208A variant nucleotide sequence.

SEQ ID NO:46 is an *E. coli* codon-optimized txp40-1 R217A variant nucleotide sequence.

SEQ ID NO:47 is an *E. coli* codon-optimized txp40-1 R226A variant nucleotide sequence.

SEQ ID NO:48 is an *E. coli* codon-optimized txp40-1 R240A variant nucleotide sequence.

SEQ ID NO:49 is an *E. coli* codon-optimized txp40-1 R252A variant nucleotide sequence.

SEQ ID NO:50 is an *E. coli* codon-optimized txp40-1 R305A variant nucleotide sequence.

SEQ ID NO:51 is an *E. coli* codon-optimized txp40-1 R311A variant nucleotide sequence.

SEQ ID NO:52 is an *E. coli* codon-optimized txp40-1 K31A/K49A variant nucleotide sequence.

SEQ ID NO:53 is an *E. coli* codon-optimized txp40-1 K31A/K333A variant nucleotide sequence.

SEQ ID NO:54 is an *E. coli* codon-optimized txp40-1 K31A/R208A variant nucleotide sequence.

SEQ ID NO:55 is an *E. coli* codon-optimized txp40-1 R208A/K333A variant nucleotide sequence.

SEQ ID NO:56 is an *E. coli* codon-optimized txp40-1 K49A/R208A variant nucleotide sequence.

SEQ ID NO:57 is an *E. coli* codon-optimized txp40-1 K49A/K333A variant nucleotide sequence.

SEQ ID NO:58 is an *E. coli* codon-optimized txp40-1 K31A/K49A/K333A variant nucleotide sequence.

SEQ ID NO:59 is an *E. coli* codon-optimized txp40-1 K31A/K49A/R208A/K333A variant nucleotide sequence.

SEQ ID NO:60 is an *E. coli* codon-optimized txp40-1 K73A/K213A variant nucleotide sequence.

SEQ ID NO:61 is an *E. coli* codon-optimized txp40-1 K103A/K213A variant nucleotide sequence.

SEQ ID NO:62 is an *E. coli* codon-optimized txp40-1 K213A/K284A variant nucleotide sequence.

SEQ ID NO:63 is an *E. coli* codon-optimized txp40-1 K31A/K49A/K213A variant nucleotide sequence.

SEQ ID NO:64 is an *E. coli* codon-optimized txp40-1 K119A/K213A variant nucleotide sequence.

SEQ ID NO:65 is an *E. coli* codon-optimized txp40-1 K213A/R167A variant nucleotide sequence.

SEQ ID NO:66 is an *E. coli* codon-optimized txp40-1 K119A/R167A variant nucleotide sequence.

SEQ ID NO:67 is an *E. coli* codon-optimized txp40-1 S11Y/M86I/K119A/K213T variant nucleotide sequence.

SEQ ID NO:68 is an *E. coli* codon-optimized txp40-1 S11Y/K119A/K213A variant nucleotide sequence.

SEQ ID NO:69 is an *E. coli* codon-optimized txp40-1 K119A/F169V/K213A variant nucleotide sequence.

SEQ ID NO:70 is an *E. coli* codon-optimized txp40-1 K119A/P134L/K213A variant nucleotide sequence.

SEQ ID NO:71 is an *E. coli* codon-optimized txp40-1 I101L/K103T/K119A/K213A/N257T variant nucleotide sequence.

SEQ ID NO:72 is an *E. coli* codon-optimized txp40-1 H62Q/D99V/K119A/T165I/R167C/K213A variant nucleotide sequence.

SEQ ID NO:73 is an *E. coli* codon-optimized txp40-1 K119A/K213A/L316V variant nucleotide sequence.

SEQ ID NO:74 is a Txp40-1 K31A variant amino acid sequence.

SEQ ID NO:75 is a Txp40-1 K48A variant amino acid sequence.

SEQ ID NO:76 is a Txp40-1 K49A variant amino acid sequence.

SEQ ID NO:77 is a Txp40-1 K73A variant amino acid sequence.

SEQ ID NO:78 is a Txp40-1 K75A variant amino acid sequence.

SEQ ID NO:79 is a Txp40-1 K103A variant amino acid sequence.

SEQ ID NO:80 is a Txp40-1 K111A variant amino acid sequence.

SEQ ID NO:81 is a Txp40-1 K119A variant amino acid sequence.

SEQ ID NO:82 is a Txp40-1 K133A variant amino acid sequence.

SEQ ID NO:83 is a Txp40-1 K143A variant nucleotide sequence.

SEQ ID NO:84 is a Txp40-1 K170A variant amino acid sequence.

SEQ ID NO:85 is a Txp40-1 K191A variant amino acid sequence.

SEQ ID NO:86 is a Txp40-1 K200A variant amino acid sequence.

SEQ ID NO:87 is a Txp40-1 K209A variant amino acid sequence.

SEQ ID NO:88 is a Txp40-1 K210A variant amino acid sequence.

SEQ ID NO:89 is a Txp40-1 K213A variant amino acid sequence.

SEQ ID NO:90 is a Txp40-1 K221A variant amino acid sequence.

SEQ ID NO:91 is a Txp40-1 K238A variant amino acid sequence.

SEQ ID NO:92 is a Txp40-1 K247A variant amino acid sequence.

SEQ ID NO:93 is a Txp40-1 K250A variant amino acid sequence.

SEQ ID NO:94 is a Txp40-1 K263A variant amino acid sequence.

SEQ ID NO:95 is a Txp40-1 K265A variant amino acid sequence.

SEQ ID NO:96 is a Txp40-1 K271A variant amino acid sequence.

SEQ ID NO:97 is a Txp40-1 K275A variant amino acid sequence.

SEQ ID NO:98 is a Txp40-1 K284A variant amino acid sequence.

SEQ ID NO:99 is a Txp40-1 K296A variant amino acid sequence.

SEQ ID NO: 100 is a Txp40-1 K309A variant amino acid sequence.

SEQ ID NO: 101 is a Txp40-1 K333A variant amino acid sequence.

SEQ ID NO:102 is a Txp40-1 R10A variant amino acid sequence.

SEQ ID NO:103 is a Txp40-1 R26A variant amino acid sequence.

SEQ ID NO:104 is a Txp40-1 R46A variant amino acid sequence.

SEQ ID NO: 105 is a Txp40-1 R167A variant amino acid sequence.

SEQ ID NO: 106 is a Txp40-1 R186A variant amino acid sequence.

SEQ ID NO: 107 is a Txp40-1 R187A variant amino acid sequence.

SEQ ID NO: 108 is a Txp40-1 R208A variant amino acid sequence.

SEQ ID NO: 109 is a Txp40-1 R217A variant amino acid sequence.

SEQ ID NO:110 is a Txp40-1 R226A variant amino acid sequence.

SEQ ID NO: 111 is a Txp40-1 R240A variant amino acid sequence.

SEQ ID NO: 112 is a Txp40-1 R252A variant amino acid sequence.

SEQ ID NO: 113 is a Txp40-1 R305A variant amino acid sequence.

SEQ ID NO: 114 is a Txp40-1 R311A variant amino acid sequence.

SEQ ID NO: 115 is a Txp40-1 K31A/K49A variant amino acid sequence.

SEQ ID NO:116 is a Txp40-1 K31A/K333A variant amino acid sequence.

SEQ ID NO:117 is a Txp40-1 K31A/R208A variant amino acid sequence.

SEQ ID NO: 118 is a Txp40-1 R208A/K333A variant amino acid sequence.

SEQ ID NO:119 is a Txp40-1 K49A/R208A variant amino acid sequence.

SEQ ID NO:120 is a Txp40-1 K49A/K333A variant amino acid sequence.

SEQ ID NO: 121 is a Txp40-1 K31A/K49A/K333A variant amino acid sequence.

SEQ ID NO: 122 is a Txp40-1 K31A/K49A/R208A/K333A variant amino acid sequence.

SEQ ID NO:123 is a Txp40-1 K73A/K213A variant amino acid sequence.

SEQ ID NO: 124 is a Txp40-1 K103A/K213A variant amino acid sequence.

SEQ ID NO: 125 is a Txp40-1 K213A/K284A variant amino acid sequence.

SEQ ID NO: 126 is a Txp40-1 K31A/K49A/K213A variant amino acid sequence.

SEQ ID NO: 127 is a Txp40-1 K119A/K213A variant amino acid sequence.

SEQ ID NO: 128 is a Txp40-1 K213A/R167A variant amino acid sequence.

SEQ ID NO: 129 is a Txp40-1 K119A/R167A variant amino acid sequence.

SEQ ID NO:130 is a Txp40-1 S11Y/M86I/K119A/K213T variant amino acid sequence.

SEQ ID NO: 131 is a Txp40-1 S11Y/K119A/K213A variant amino acid sequence.

SEQ ID NO: 132 is a Txp40-1 K119A/F169V/K213A variant amino acid sequence.

SEQ ID NO:133 is a Txp40-1 K119/P134L/K213A variant amino acid sequence.

SEQ ID NO:134 is a Txp40-1 I101L/K103T/K119A/K213A/N257T variant amino acid sequence.

SEQ ID NO:135 is a Txp40-1 H62Q/D99V/K119A/T165I/R167C/K213A variant amino acid sequence.

SEQ ID NO:136 is a K119A/K213A/L316V variant amino acid sequence.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Nucleotide sequences provided herein are presented in the 5' to 3' direction, from left to right and are presented using the standard code for representing nucleotide bases as set forth in 37 CFR §§ 1.821-1.825 and the World Intellectual Property Organization (WIPO) Standard ST.25, for example: adenine (A), cytosine (C), thymine (T), and guanine (G).

Amino acids are likewise indicated using the WIPO Standard ST.25, for example: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Definitions

For clarity, certain terms used in the specification are defined and presented as follows:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20, ±10, ±5, ±1, ±0.5, or even ±0.1 of the specified amount. As used herein, phrases such as "between about X and Y" mean "between about X and about Y" and phrases such as "from about X to Y" mean "from about X to about Y."

As used herein, phrases such as "from X to Y" should be interpreted to include X and Y, unless the context indicates otherwise.

"Activity" of the insecticidal proteins of the invention is meant that the insecticidal proteins function as orally active insect control agents, have a toxic effect, and/or are able to disrupt or deter insect feeding, which may or may not cause death of the insect. When an insecticidal protein of the invention is delivered to the insect, the result is typically death of the insect, or the insect does not feed upon the source that makes the insecticidal protein available to the insect. "Pesticidal" is defined as a toxic biological activity capable of controlling a pest, such as an insect, nematode, fungus, bacteria, or virus, preferably by killing or destroying them. "Insecticidal" is defined as a toxic biological activity capable of controlling insects, preferably by killing them. A "pesticidal agent" is an agent that has pesticidal activity. An "insecticidal agent" is an agent that has insecticidal activity.

"Associated with/operatively linked" refer to two nucleic acids that are related physically or functionally. For example, a promoter or regulatory DNA sequence is said to be "associated with" a DNA sequence that codes for RNA or a protein if the two sequences are operatively linked or situated such that the regulatory DNA sequence will affect the expression level of the coding or structural DNA sequence.

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence wherein the codons are chosen to reflect the particular codon bias that a host cell or organism may have. This is typically done in such a way so as to preserve the amino acid sequence of the polypeptide encoded by the nucleotide sequence to be optimized. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

To "control" insects means to inhibit, through a toxic effect, the ability of insect pests to survive, grow, feed, and/or reproduce, or to limit insect-related damage or loss in crop plants. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim" and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of variant or homolog Cry proteins are aligned with each other, the amino acids that "correspond to" certain enumerated positions in the variant or homolog protein are those that align with these positions in a reference protein but that are not necessarily in these exact numerical positions relative to the particular reference amino acid sequence of the invention. For example, if SEQ ID NO:1 is the reference sequence and is aligned with SEQ ID NO:10, the Gly51 of SEQ ID NO: 10 "corresponds to" Gly42 of SEQ ID NO:1, or for example, the Val59 of SEQ ID NO:10 "corresponds to" the Ile50 of SEQ ID NO:1.

As used herein, the term "Cry protein" means an insecticidal protein of a *Bacillus thuringiensis* crystal delta-endotoxin type. The term "Cry protein" can refer to the protoxin form or any bio-active fragment or toxin thereof including partially processed and the mature toxin form, e.g., without the N-terminal peptidyl fragment and/or the C-terminal protoxin tail.

To "deliver" an insecticidal protein means that the insecticidal protein comes in contact with an insect, resulting in a toxic effect and control of the insect. The insecticidal protein may be delivered in many recognized ways, e.g., through a transgenic plant expressing the insecticidal protein, formulated protein composition(s), sprayable protein composition(s), a bait matrix, or any other art-recognized toxin delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of an insecticidal protein that inhibits, through a toxic effect, the ability of insects to survive, grow, feed and/or reproduce, or to limit insect-related damage or loss in crop plants. "Effective insect-controlling amount" may or may not mean killing the insects, although it preferably means killing the insects.

"Expression cassette" as used herein means a nucleic acid sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may have at least one of its components heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development.

An expression cassette comprising a nucleotide sequence of interest may be chimeric, meaning that at least one of its components is heterologous with respect to at least one of its other components. An expression cassette may also be one that comprises a native promoter driving its native gene; however, it has been obtained in a recombinant form useful for heterologous expression. Such usage of an expression cassette means that the expression cassette is not naturally occurring in the cell into which it has been introduced.

An expression cassette also can optionally include a transcriptional and/or translational termination region (i.e., termination region) that is functional in plants. A variety of transcriptional terminators are available for use in expression cassettes and are responsible for the termination of transcription beyond the heterologous nucleotide sequence of interest and correct mRNA polyadenylation. The termination region may be native to the transcriptional initiation region, may be native to the operably linked nucleotide sequence of interest, may be native to the plant host, or may be derived from another source (i.e., foreign or heterologous to the promoter, the nucleotide sequence of interest, the plant host, or any combination thereof). Appropriate transcriptional terminators include, but are not limited to, the CAMV 35S terminator, the tm1 terminator, the nopaline synthase terminator and/or the pea rbcs E9 terminator. These can be used in both monocotyledons and dicotyledons. In addition, a coding sequence's native transcription terminator can be used. Any available terminator known to function in plants can be used in the context of this invention.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (e.g. if a gene encodes a protein), through "translation" of mRNA. Gene expression can be regulated at many stages in the process. For example, in the case of antisense or dsRNA constructs, respectively, expression may refer to the transcription of the antisense RNA only or the dsRNA only. In embodiments, "expression" refers to the transcription and stable accumulation of sense (mRNA) or functional RNA. "Expression" may also refer to the production of protein.

A "gene" is a defined region that is located within a genome and comprises a coding nucleic acid sequence and typically also comprises other, primarily regulatory, nucleic acids responsible for the control of the expression, that is to say the transcription and translation, of the coding portion. A gene may also comprise other 5' and 3' untranslated sequences and termination sequences. Further elements that may be present are, for example, introns. The regulatory nucleic acid sequence of the gene may not normally be operatively linked to the associated nucleic acid sequence as found in nature and thus would be a chimeric gene.

"Gene of interest" refers to any nucleic acid molecule which, when transferred to a plant, confers upon the plant a desired trait such as antibiotic resistance, virus resistance, insect resistance, disease resistance, or resistance to other pests, herbicide tolerance, abiotic stress tolerance, male sterility, modified fatty acid metabolism, modified carbohydrate metabolism, improved nutritional value, improved performance in an industrial process or altered reproductive capability. The "gene of interest" may also be one that is transferred to plants for the production of commercially valuable enzymes or metabolites in the plant.

A "gut protease" is a protease naturally found in the digestive tract of an insect. This protease is usually involved in the digestion of ingested proteins. Examples of gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y).

A "heterologous" nucleic acid sequence or nucleic acid molecule is a nucleic acid sequence or nucleic acid molecule not naturally associated with a host cell into which it is introduced, including non-naturally occurring multiple copies of a naturally occurring nucleic acid sequence. A heterologous nucleic acid sequence or nucleic acid molecule may comprise a chimeric sequence such as a chimeric expression cassette, where the promoter and the coding region are derived from multiple source organisms. The promoter sequence may be a constitutive promoter sequence, a tissue-specific promoter sequence, a chemically-inducible promoter sequence, a wound-inducible promoter sequence, a stress-inducible promoter sequence, or a developmental stage-specific promoter sequence.

A "homologous" nucleic acid sequence is a nucleic acid sequence naturally associated with a host cell into which it is introduced.

"Homologous recombination" is the reciprocal exchange of nucleic acid fragments between homologous nucleic acid molecules.

"Identity" or "percent identity" refers to the degree of similarity between two nucleotide or amino acid sequences. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. The phrase "substantially identical," in the context of two nucleotide or two amino acid sequences, refers to two or more sequences or subsequences that have at least about 50 nucleotide or amino acid residue identity when compared and aligned for maximum correspondence as measured using one of the following sequence comparison algorithms or by visual inspection. In certain embodiments, substantially identical sequences have at least about 60, or at least about 70, or at least about 80, or at least about 85, or even at least about 90 or 95 nucleotide or amino acid residue identity. In certain embodiments, substantial identity exists over a region of the sequences that is at least about 50 residues in length, or over a region of at least about 100 residues, or the sequences are substantially identical over at least about 150 residues. In further embodiments, the sequences are substantially identical when they are identical over the entire length of the coding regions.

Optimal alignment of sequences for comparison can be conducted, e.g., by the local homology algorithm of Smith & Waterman, *Adv. Appl. Math.* 2: 482 (1981), by the homology alignment algorithm of Needleman & Wunsch, *J. Mol. Biol.* 48: 443 (1970), by the search for similarity method of Pearson & Lipman, *Proc. Nat'l. Acad. Sci. USA* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection (see generally, Ausubel et al., infra).

One example of an algorithm that is suitable for determining percent sequence identity and sequence similarity is the BLAST algorithm, which is described in Altschul et al., *J. Mol. Biol.* 215: 403-410 (1990). Software for performing BLAST analyses is publicly available through the National Center for Biotechnology Information (http://www.ncbi.nln-.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another widely used and accepted computer program for performing sequence alignments is CLUSTALW v1.6 (Thompson, et al. Nuc. Acids Res., 22: 4673-4680, 1994). The number of matching bases or amino acids is divided by the total number of bases or amino acids, and multiplied by 100 to obtain a percent identity. For example, if two 580 base pair sequences had 145 matched bases, they would be 25 percent identical. If the two compared sequences are of different lengths, the number of matches is divided by the shorter of the two lengths. For example, if there were 100 matched amino acids between a 200 and a 400 amino acid proteins, they are 50 percent identical with respect to the shorter sequence. If the shorter sequence is less than 150 bases or 50 amino acids in length, the number of matches are divided by 150 (for nucleic acid bases) or 50 (for amino acids), and multiplied by 100 to obtain a percent identity.

Another indication that two nucleic acids are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50 of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50 formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7 sodium dodecyl sulfate (SDS), 0.5 M $NaPO_4$, 1 mM EDTA at 50° C. with washing in 2×SSC, 0.1 SDS at 50° C., more desirably in 7 sodium dodecyl sulfate (SDS), 0.5 M $NaPO_4$, 1 mM EDTA at 50° C. with washing in 1×SSC, 0.1 SDS at 50° C., more desirably still in 7 sodium dodecyl sulfate (SDS), 0.5 M $NaPO_4$, 1 mM EDTA at 50° C. with washing in 0.5×SSC, 0.1 SDS at 50° C., preferably in 7 sodium dodecyl sulfate (SDS), 0.5 M $NaPO_4$, 1 mM EDTA at 50° C. with washing in 0.1×SSC, 0.1 SDS at 50° C., more preferably in 7 sodium dodecyl sulfate (SDS), 0.5 M $NaPO_4$, 1 mM EDTA at 50° C. with washing in 0.1×SSC, 0.1 SDS at 65° C.

A further indication that two nucleic acids or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

A nucleotide sequence is "isocoding with" a reference nucleotide sequence when the nucleotide sequence encodes a polypeptide having the same amino acid sequence as the polypeptide encoded by the reference nucleotide sequence.

An "isolated" nucleic acid molecule, or isolated polynucleotide or an isolated Txp40 protein is a nucleic acid molecule, or polynucleotide or protein that, by the hand of man, exists apart from its native environment and is therefore not a product of nature. An isolated nucleic acid molecule, or polynucleotide or protein may exist in a purified form or may exist in a non-native environment such as, for example without limitation, a recombinant microbial cell, plant cell, plant tissue, or plant.

The term "motif" or "consensus sequence" or "signature" refers to a short, conserved region in the sequence of evolutionarily related proteins. Motifs are frequently highly conserved parts of domains, but may also include only part of the domain, or be located outside of conserved domain (if all of the amino acids of the motif fall outside of a defined domain).

A "native" or "wild type" nucleic acid, polynucleotide, nucleotide sequence, polypeptide or amino acid sequence refers to a naturally occurring or endogenous nucleic acid, polynucleotide, nucleotide sequence, polypeptide or amino acid sequence.

A "nucleic acid molecule" or "nucleotide sequence" is a segment of single- or double-stranded DNA or RNA that can be isolated from any source. In the context of the present invention, the nucleic acid molecule is typically a segment of DNA. In some embodiments, the nucleic acid molecules of the invention are isolated nucleic acid molecules.

The terms "nucleic acid molecule," and "polynucleotide" may be used interchangeably herein.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

The terms "protein," "peptide" and "polypeptide" are used interchangeably herein.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

A "portion" or "fragment" of a polypeptide of the invention will be understood to mean an amino acid sequence of reduced length relative to a reference amino acid sequence of a polypeptide of the invention. Such a portion or fragment according to the invention may be, where appropriate, included in a larger polypeptide of which it is a constituent (e.g., a tagged or fusion protein). In embodiments, the "portion" or "fragment" substantially retains insecticidal activity (e.g., at least 40, 50, 60, 70, 80, 85, 90, 95 or even 100 of the activity of the full-length protein, or has even greater insecticidal activity than the full-length protein).

A "promoter" is an untranslated DNA sequence upstream of the coding region that contains the binding site for RNA polymerase and initiates transcription of the DNA. The promoter region may also include other elements that act as regulators of gene expression.

As used herein, the term "recombinant" refers to a form of nucleic acid (e.g., DNA or RNA) or protein or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized, for example, a polynucleotide synthesize using an assembled nucleotide sequence, and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. Another example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule incorporated into its genome. As a result of such genomic alteration, the recombinant plant is distinctly different from the related wild-type plant.

The terms "reduce," "reduced," "reducing," "reduction," "diminish," and "suppress" (and grammatical variations thereof) and similar terms, as used herein, refer to a decrease in the survival, growth and/or reproduction of a plant pest, e.g., by contacting a plant with a polypeptide of the invention (such as, for example, by transgenic expression or by topical application methods). This decrease in survival, growth and/or reproduction can be in reference to the level observed in the absence of the polypeptide of the invention (e.g., a plant that is not transgenically expressing the polypeptide or is not topically treated with the polypeptide). Thus, in embodiments, the terms "reduce," "reduced," "reducing," "reduction," "diminish," and "suppress" (and grammatical variations thereof) and similar terms mean a decrease of at least about 5, 10, 15, 20, 25, 30, 35, 40, 45, 50, 55, 60, 65, 70, 75, 80, 85, 90, 95 or more as compared with a plant that is not contacted with a polypeptide of the invention (e.g., a plant that is not transgenically expressing the polypeptide or is not topically treated with the polypeptide). In representative embodiments, the reduction results in no or essentially no (i.e., an insignificant amount, e.g., less than about 10, less than about 5 or even less than about 1) detectable survival, growth and/or reproduction of the plant pest.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

"Transformation" is a process for introducing heterologous nucleic acid into a host cell or organism. In particular embodiments, "transformation" means the stable integration of a DNA molecule into the genome (nuclear or plastid) of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

As used herein, a "Txp40 protein" is a naturally occurring toxin produced by two genera of bacteria, *Xenorhabdus* and *Photorhabdus*, which symbiotically associate with the nematode genera, *Steinernema* and *Heterrhabditis*, respectively. The nematode-bacteria pair are capable of invading and killing certain insects. A Txp40 protein was first isolated from *P. luminescens* and shown to have injectable toxicity to several insect pests.

A "variant Txp40 protein" according to the invention means a non-naturally occurring engineered protein having at least 95% identity to SEQ ID NO:1 that is orally toxic to a *Spodoptera* insect pest, particularly to a fall armyworm pest (*Spodoptera frugiperda*).

The invention relates to Txp40 insecticidal proteins that are shown herein to surprisingly have oral toxicity to *Spodoptera frugiperda* (fall armyworm, FAW), an insect pest species that is recalcitrant to many classes of insecticidal proteins, including Cry proteins derived from *Bacillus thuringiensis* (Bt). Although Txp40 proteins are known in the art, because of their natural biology, they have been shown to be insecticidal to certain insects primarily by direct injection into the insect's haemocoel (See for example, U.S. Pat. No. 6,630,619; Park et. al. 2012. J. Agric. Food Chem. 60:4053-4059 and Brown et. al. 2006. App. Environ. Microbiol. 72:1653-1662). Such direct injection mimics the natural pathway that Txp40 proteins are delivered to insects via pathogenic nematodes, for example, entomopathogenic nematodes in the families Heterorhabditidae and Steinernematiidae, that first invade the target insect haemocoel and release pathogenic bacteria, for example *Photorhabdus* and *Xenorhabdus* bacteria, that produce the Txp40 proteins. One group has reported oral toxicity of a Txp40 protein only against the greater wax moth, *Galleria mellonella* (Mathur et al. 2018. Toxicon 154:59-73), an insect that is not a crop pest and one that is highly susceptible to many classes of insecticidal proteins, including highly susceptible to many Cry proteins. The instant invention is the first known disclosure of the oral toxicity of a Txp40 protein to FAW insect pests. Thus, the invention provides novel methods of controlling FAW pest populations using a Txp40 insecticidal protein and variants of a Txp40 protein. The novel methods of the invention are particularly useful for controlling FAW populations that are or may become resistant to other insect control agents such as the Cry proteins and/or Vip3 proteins.

Accordingly, in some embodiments, the invention provides a method of controlling a *Spodoptera* insect pest, comprising contacting the *Spodoptera* insect pest with a Txp40 protein comprising, consisting essentially of or consisting of an amino acid sequence having at least 95% identity to SEQ ID NO:1. In other embodiments, the Txp40 protein comprises, consists essentially of or consists of an amino acid sequence that has at least 95%, or at least 96%, or at least 97%, or at least 98%, or at least 99% identity across its entire length to SEQ ID NO:1. In other embodiments, the Txp40 protein comprises, consists essentially of or consists of SEQ ID NO: 1, SEQ ID NO:2 or any of SEQ ID NOs: 74-136. In other embodiments, the method comprises delivering, for example orally delivering, to the *Spodoptera* insect pest or an environment thereof an effective amount of a Txp40 protein of the invention. Generally, to be effective, the Txp40 protein is orally ingested by the *Spodoptera* insect pest. Examples of ways to deliver a Txp40 protein of the invention orally to a *Spodoptera* insect pest include, but are not limited to, providing the protein (1) in a transgenic plant, wherein the insect eats (ingests) one or more parts of the transgenic plant, thereby ingesting the Txp40 polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to a *Spodoptera* insect pest can be used to deliver the toxic proteins of the invention. In some particular embodiments, the Txp40 insecticidal protein of the invention is delivered orally to a *Spodoptera* insect pest, for example, where the insect ingests one or more parts of a transgenic plant of the invention. In further embodiments, the *Spodoptera* insect pest is *Spodoptera frugiperda* (fall armyworm, FAW).

In other embodiments, a Txp40 insecticidal protein of the invention is delivered orally to a *Spodoptera* insect pest, for example a fall armyworm insect (*Spodoptera frugiperda*), wherein the insect ingests one or more parts of a plant sprayed with a composition comprising the Txp40 insecticidal protein of the invention. Delivering the composition of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with a compound(s), composition(s) or formulation(s) are well-known to those of skill in the art.

In further embodiments, the invention provides a method of controlling a FAW insect pest or pest population that is resistant to a Cry protein and/or a vegetative insecticidal protein, for example Vip3, comprising delivering to the FAW pest or pest population, or an environment thereof, an effective amount of a Txp40 protein or composition of the invention. In some embodiments, the Txp40 protein comprises, consists essentially of or consists of an amino acid sequence having at least 95% identity to SEQ ID NO:1. In other embodiments, the Txp40 protein comprises, consists essentially of or consists of an amino acid sequence that has at least 95%, or at least 96%, or at least 97%, or at least 98%, or at least 99% identity across its entire length to SEQ ID NO:1. In other embodiments, the amino acid sequence of the Txp40 protein comprises, consists essentially of or consists of SEQ ID NO:1, SEQ ID NO:2 or any of SEQ ID NOs: 74-136. In other embodiments, the Vip3 is a Vip3A protein. In other embodiments, the Vip3A protein is a Vip3Aa20 protein expressed in corn plants comprising transgenic event MIR162. In still other embodiments, the Cry protein is a Cry1A, a Cry1B, a Cry1C, a Cry1D, a Cry1F, a Cry1J or a Cry2A protein. In further embodiments, the Cry1F protein is a Cry1Fa protein expressed in corn plants comprising the transgenic event TC1507.

In other embodiments, the invention provides a method of preventing the development of resistance in a population of *Spodoptera* insect pests, for example fall armyworm, to a Cry protein and/or a Vip3 protein expressed in a transgenic plant, the method comprising delivering to the target *Spodoptera* population a transgenic plant comprising a polynucleotide comprising a nucleotide sequence encoding a Vip3 protein and/or a nucleotide sequence encoding a Cry protein; and a polynucleotide expression cassette or vector of the invention that expresses a Txp40 insecticidal protein of the invention. In other embodiments, the Vip3 protein is a Vip3A protein. In other embodiments, the Vip3A protein is a Vip3Aa20 protein. In still other embodiments, the Cry protein is a Cry1A, a Cry1B, a Cry1C, a Cry1D, a Cry1F, a Cry1J or a Cry2A protein. In further embodiments, the Cry1F protein is a Cry1Fa protein. In still other embodiments, the transgenic plant is a corn plant that comprises event MIR162 and/or event TC1507. In some embodiments, the Txp40 protein comprises, consists essentially of or consists of an amino acid sequence that has at least 95% identity across its full length with SEQ ID NO:1. In another embodiment, the Txp40 protein comprises, consists essentially of or consists of the amino acid sequence of SEQ ID NO:1, SEQ ID NO:2 or any of SEQ ID NOs: 74-136. According to foregoing embodiments, the transgenic plant can comprise a breeding stack of two or more genes encoding a Txp40 insecticidal protein of the invention, a molecular stack of two or more genes encoding a Txp40 insecticidal protein of the invention, or a combination of both.

The invention also provides a variant Txp40 insecticidal protein comprising, consisting essentially of or consisting of an amino acid sequence that has at least 95%, 96%, 97%, 98%, 99%, 99.1%, 99.2%, 99.3%, 99.4%, 99.5%, 99.6%, 99.7%, 99.8% or 99.9% identity to SEQ ID NO:1, wherein the variant Txp40 protein has oral activity to a *Spodoptera* insect pest, particularly to a *Spodoptera frugiperda* (fall armyworm, FAW) insect pest. In some embodiments, a variant Txp40 protein of the invention comprises, consists essentially of or consists of the amino acid sequence of SEQ ID NO:2 or any of SEQ ID NOs:74-136.

In some embodiments, the invention provides a variant Txp40 insecticidal protein that has at least 95%, 96%, 97%, 98%, 99%, 99.1%, 99.2%, 99.3%, 99.4%, 99.5%, 99.6%, 99.7%, 99.8% or 99.9% identity to SEQ ID NO:1 and has an amino acid substitution compared to SEQ ID NO: 1. In other embodiments, the invention provides a variant Txp40 insecticidal protein that has at least 95%, 96%, 97%, 98%, 99%, 99.1%, 99.2%, 99.3%, 99.4%, 99.5%, 99.6%, 99.7%, 99.8% or 99.9% identity to SEQ ID NO:1 and has an amino acid substitution compared to SEQ ID NO:1 at a position corresponding to amino acid position 10, 11, 26, 31, 38, 46, 48, 49, 73, 75, 86, 96, 101, 103, 111, 116, 119, 133, 134, 143, 155, 167, 169, 170, 182, 186, 187, 191, 200, 208, 209, 210, 213, 217, 221, 226, 238, 240, 247, 250, 252, 256, 257, 263, 265, 266, 271, 275, 284, 293, 296, 305, 308, 309, 311, 313, 315, 320, 326, 328, or 333 of SEQ ID NO:1, or any combination thereof.

In some embodiments, the invention provides a variant Txp40 insecticidal protein that has at least 95%, 96%, 97%, 98%, 99%, 99.1%, 99.2%, 99.3%, 99.4%, 99.5%, 99.6%, 99.7%, 99.8% or 99.9% identity to SEQ ID NO:1 and has an amino acid substitution compared to SEQ ID NO:1 at a position corresponding to amino acid position 119 and/or 213 of SEQ ID NO:1. In other embodiments, the variant Txp40 protein has an A at a position corresponding to amino acid position 119 and/or has an A at a position corresponding to amino acid position 213 of SEQ ID NO:1. In other embodiments, the variant Txp40 protein has a K119A and/or a K213A substitution in SEQ ID NO:1. In other embodiments, the variant Txp40 protein comprises, consists essentially of or consists of the amino acid sequence of SEQ ID NO:18, SEQ ID NO:26 or SEQ ID NO:127.

In some embodiments, the invention provides a variant Txp40 insecticidal protein that has at least 95%, 96%, 97%, 98%, 99%, 99.1%, 99.2%, 99.3%, 99.4%, 99.5%, 99.6%, 99.7%, 99.8% or 99.9% identity to SEQ ID NO:1 and has an amino acid substitution compared to SEQ ID NO:1 at a position corresponding to amino acid position 11, 119 and/or 213 of SEQ ID NO:1. In other embodiments, the variant Txp40 protein has an Y at a position corresponding to amino acid position 11 of SEQ ID NO:1, an A at an amino acid position corresponding to amino acid position 119 of SEQ ID NO:1 and/or an A at an amino acid position corresponding to amino acid position 213 of SEQ ID NO:1. In other embodiments, the variant Txp40 protein is SEQ ID NO:1, wherein the amino acid S at position 11 has been substituted with a Y, the amino acid K at position 119 has been substituted with an A and/or the amino acid K at position 213 has been substituted with an A. In other embodiments, the variant Txp40 protein comprises, consists essentially of or consists of the amino acid sequence of SEQ ID NO:131.

It is recognized that nucleotide sequences that encode a Txp40 protein of the invention may be altered by various methods, and that these alterations may result in nucleotide sequences encoding variant Txp40 proteins with amino acid sequences different than that encoded by a naturally occurring Txp40 protein. A Txp40 protein may be altered in various ways including amino acid substitutions, deletions, truncations, and insertions of one or more amino acids of SEQ ID NO:1, including up to about 2, about 3, about 4, about 5, about 6, about 7, about 8, about 9, about 10, about 15, about 17, or about 20 amino acid substitutions, deletions or insertions. Methods for such manipulations are generally known in the art. For example, amino acid sequence variants of a native Txp40 protein can be prepared by mutations in a polynucleotide that encodes the Txp40 protein. This may also be accomplished by one of several forms of mutagenesis or in directed evolution. In some embodiments, the changes encoded in the amino acid sequence will not substantially affect the function of the protein. Such variants will possess the desired insecticidal activity. In other embodiments, the resulting variant Txp40 protein will have increased insecticidal activity compared to the wild-type Txp40 protein, particularly against *Spodoptera* insect pests. In other embodiments, the resulting variant protein is encoded by a synthetic variant polynucleotide. In still other embodiments, the Txp40 protein of the invention is encoded by a nucleic acid molecule comprising, consisting essentially of or consisting of the nucleotide sequence of any of SEQ ID NOs: 11-73.

According to some embodiments, the invention provides a synthetic polynucleotide comprising, consisting essentially of or consisting of a nucleotide sequence encoding a Txp40 protein of the invention that is orally toxic to a *Spodoptera* pest, in particular to fall armyworm, wherein the nucleotide sequence has codons optimized for expression in a transgenic organism. In other embodiments, the transgenic organism is a transgenic bacteria or a transgenic plant. In further embodiments, the transgenic plant is transgenic corn plant. Although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, it is known in the art that high expression in plants, for example corn plants, can be achieved from coding sequences that have at least about 35 GC content, or at least about 45, or at least about 50, or at least about 60. Microbial nucleotide sequences that have low GC contents may express poorly in plants. Although certain nucleotide sequences can be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, in embodiments, the nucleotide sequence is modified to remove illegitimate splice sites that may cause message truncation. Such modifications to the nucleotide sequences can be made using well known techniques of site directed mutagenesis, PCR, and synthetic gene construction using the methods described, for example, in U.S. Pat. Nos. 5,625,136; 5,500,365 and 6,013,523. In some embodiments of the invention, the codon-optimized nucleotide sequence of the invention comprises, consists essentially of or consists of a nucleotide sequence having at least 50, 55, 60 or at least 65 GC content. In still other embodiments the codon-optimized nucleotide sequence comprises, consists essentially of or consists of the nucleotide sequence of SEQ ID NO:4, SEQ ID NO:5 or any of SEQ ID NOs: 11-73. The skilled person will recognize that such GC content may be achieved in a number of different ways. For example, such synthetic coding sequences or polynucleotides are made according to the procedure disclosed in U.S. Pat. No. 5,625,136. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989). It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

In some embodiments of the invention, a chimeric gene is provided that comprises a promoter operably linked to a heterologous nucleic acid molecule comprising a nucleotide sequence that encodes a Txp40 protein that has insecticidal activity to a *Spodoptera* insect pest, wherein the nucleotide sequence: (a) is any of SEQ ID NOs: 3-5 or 11-73; (b) has at least 95% identity to any of SEQ ID NOs: 3-5 or 11-73;

(c) encodes a protein comprising the amino acid sequence of any of SEQ ID NOs: 1, 2 or 74-136; (d) encodes a protein comprising an amino acid sequence that has at least 95% identity to SEQ ID NO:1; or (e) is complementary to the nucleotide sequence of any one of (a) to (d).

In some embodiments, the nucleic acid molecule comprises a maize codon-optimized nucleotide sequence. In other embodiments, the promoter is a plant-expressible promoter, particularly a promoter that expresses in maize plants. For example, without limitation, the plant-expressible promoter can be selected from the group of promoters consisting of ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

Although many promoters from dicotyledons have been shown to be operational in monocotyledons and vice versa, in embodiments, dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

The choice of promoter can vary depending on the temporal and spatial requirements for expression, and also depending on the host cell to be transformed. Thus, for example, expression of the nucleotide sequences of the invention can be in any plant and/or plant part, (e.g., in leaves, in stalks or stems, in ears, in inflorescences (e.g., spikes, panicles, cobs, etc.), in roots, seeds and/or seedlings, and the like). For example, where expression in a specific tissue or organ is desired, a tissue-specific or tissue-preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells of a plant a constitutive promoter can be chosen.

Promoters useful with the invention include, but are not limited to, those that drive expression of a nucleotide sequence constitutively, those that drive expression when induced, and those that drive expression in a tissue- or developmentally-specific manner. These various types of promoters are known in the art.

Suitable constitutive promoters include, for example, CaMV 35S promoter (Odell et al., Nature 313:810-812, 1985); Arabidopsis At6669 promoter (see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO:1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Tissue-specific or tissue-preferential promoters useful for the expression of the polypeptides of the invention in plants, optionally maize, include those that direct expression in root, pith, leaf or pollen. Suitable tissue-specific promoters include, but not limited to, leaf-specific promoters (such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993), seed-preferred promoters (e.g., from seed specific genes; Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson et al., Plant Mol. Biol. 18: 235-245, 1992), legumin (Ellis, et al. Plant Mol. Biol. 10: 203-214, 1988), Glutelin (Takaiwa, et al., Mol. Gen. Genet. 208: 15-22, 1986; Takaiwa, et al., FEBS Letts. 221: 43-47, 1987), Zein (Matzke et al., Plant Mol Biol, 143). 323-32 1990), napA (Stalberg, et al., Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters (e.g., wheat LMW and HMW, glutenin-1 (Mol Gen Genet 216: 81-90, 1989; NAR 17:461-2), wheat a, b and g gliadins (EMB03:1409-15, 1984), Barley ltrl promoter, barley B1, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters (e.g., rice OSH1; Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)] flower-specific promoters, for example, AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, and promoters specific for plant reproductive tissues (e.g., OsMADS promoters; U.S. Patent Publication 2007/0006344).

Examples of promoters suitable for preferential expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition, promoters functional in plastids can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in a plant through the application of an exogenous chemical regulator. Regulation of the expression of nucleotide sequences of the invention via promoters that are chemically regulated enables the polypeptides of the invention to be synthesized only when the crop plants are treated with the inducing chemicals. Depending upon the objective, the promoter may be a chemical-inducible promoter, where application of a chemical induces gene expression, or a chemical-repressible promoter, where application of the chemical represses gene expression. Examples of such technology for chemical induction of gene expression is detailed in published application EP 0 332 104 and U.S. Pat. No. 5,614,395.

Chemical inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1 a promoter, which is activated by salicylic acid (e.g., the PR1a system), steroid steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395. Chemical induction of gene expression is also detailed in EP 0 332 104 (to Ciba-Geigy) and U.S. Pat. No. 5,614,395.

Another category of promoters useful in the invention are wound inducible promoters. Numerous promoters have been described that are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

In addition to the promoters operatively associated with the nucleotide sequences of the invention, an expression cassette of this invention can also include other regulatory elements. Regulatory elements include, but are not limited to, enhancers, introns, translation leader sequences, termination signals, and polyadenylation signal sequences. Examples of suitable transcription terminator signals are available and known in the art (e.g., tml from CaMV, E9 from rbcS). Any available terminator known to function in plants can be used in the context of this invention.

Numerous other sequences can be incorporated into the chimeric genes described in this invention. These include sequences that have been shown to enhance expression such as intron sequences (e.g., from Adhl and bronzel) and viral leader sequences (e.g., from TMV, MCMV and AMV).

For more efficient initiation of translation, sequences adjacent to the initiating methionine may be modified. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

In some embodiments, it may be desired to target expression of the polypeptides of the present invention to a specific cellular location in the plant cell. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments. For example, amino terminal sequences can be responsible for targeting a protein of interest to a cell compartment, such as, a vacuole, mitochondrion, peroxisome, protein bodies, endoplasmic reticulum, chloroplast, starch granule, amyloplast, apoplast or cell wall of a plant cell (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxyl terminal sequences are responsible for vacuolar targeting of gene products and can be used with the present invention (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases, this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

A chimeric gene of the invention also can include a nucleotide sequence for a selectable marker, which can be used to select a transformed plant, plant part and/or plant cell. Many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) Mol. Gen. Genet. 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) Biotech. 6:915-922); a nucleotide sequence encoding a nitrilase such as bxn from *Klebsiella ozaenae* that confers resistance to bromoxynil (Stalker et al. (1988) Science 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) J. Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: Chromosome Structure and Function: Impact of New Concepts, 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) Proc. Natl. Acad. Sci. USA 75:3737-3741); a nucleotide sequence encoding xylE that encodes a catechol dioxygenase (Zukowsky et al. (1983) Proc. Natl. Acad. Sci. USA 80:1101-1105); a nucleotide sequence encoding tyrosinase, an enzyme capable of oxidizing tyrosine to DOPA and dopaquinone, which in turn condenses to form melanin (Katz et al. (1983) J. Gen. Microbiol. 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding aequorin which may be employed in calcium-sensitive bioluminescence detection (Prasher et al. (1985) Biochem. Biophys. Res. Comm. 126:1259-1268); or a nucleotide sequence encoding green fluorescent protein (Niedz et al. (1995) Plant Cell Reports 14:403-406). One of skill in the art can choose a suitable selectable marker for use in an expression cassette of this invention.

In some embodiments, a chimeric gene of the invention also can include polynucleotides that encode other desired traits in addition to the chimeric insecticidal proteins of the invention. Examples of such other polynucleotides include that those encode a polypeptide or a dsRNA for the other desired trait(s) of interest. Such expression cassettes comprising the "stacked" traits may be used, e.g., to create plants, plant parts or plant cells having a desired phenotype with the stacked traits (i.e., molecular stacking). Such stacked combinations in plants can also be created by other methods including, but not limited to, cross breeding plants by any conventional methodology (i.e., a breeding stack). If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

In representative embodiments, the chimeric gene can also include an additional coding sequence for one or more polypeptides or double stranded RNA molecules (dsRNA) of interest for an agronomic trait (e.g., an agronomic trait that is primarily of benefit to a seed company, grower or grain processor). A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. In embodiments, the polypeptide of interest can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.).

Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903, 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase). See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). In embodiments, the polypeptide is a lepidopteran-active, coleopteran-active, hemipteran-active and/or dipteran-active polypeptide, or any combination thereof. It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like, and any combination of the foregoing Bt insecticidal proteins. A full list of Bt-derived proteins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

In embodiments, an additional polypeptide is an insecticidal polypeptide derived from a non-Bt source, including without limitation, an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin.

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) Foundation for Biotechnical and Industrial Fermentation Research 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) Enzyme Microb. Technol. 14:566; Torronen et al. (1992) Bio/Technology 10:1461; and Xu et al. (1998) Appl. Microbiol. Biotechnol. 49:718).

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as alpha-amylases (EC 3.2.1.1), glucuronidases (E.C. 3.2.1.131); exo-1,4-alpha-D glucanases such as amyloglucosidases and glucoamylase (EC 3.2.1.3), beta-amylases (EC 3.2.1.2), alpha-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-beta-D-glucanase (EC 3.2.1.39), beta-glucosidase (EC 3.2.1.21); c) L-arabinases, such as endo-1,5-alpha-L-arabinase (EC 3.2.1.99), alpha-arabinosidases (EC 3.2.1.55) and the like; d) galactanases such as endo-1,4-beta-D-galactanase (EC 3.2.1.89), endo-1,3-beta-D-galactanase (EC 3.2.1.90), alpha-galactosidase (EC 3.2.1.22), beta-galactosidase (EC 3.2.1.23) and the like; e) mannanases, such as endo-1,4-beta-D-mannanase (EC 3.2.1.78), beta-mannosidase (EC 3.2.1.25), alpha-mannosidase (EC 3.2.1.24) and the like; f) xylanases, such as endo-1,4-beta-xylanase (EC 3.2.1.8), beta-D-xylosidase (EC 3.2.1.37), 1,3-beta-D-xylanase, and the like; and g) other enzymes such as alpha-L-fucosidase (EC 3.2.1.51), alpha-L-rhamnosidase (EC 3.2.1.40), levanase (EC 3.2.1.65), inulanase (EC 3.2.1.7), and the like. In one embodiment, the alpha-amylase is the synthetic alpha-amylase, Amy797E, described is U.S. Pat. No. 8,093,453.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g., E.C. 3.1.1.74).

Double stranded RNA (dsRNA) molecules useful with the invention include, but are not limited to those that suppress target pest (e.g., insect) genes. In embodiments, the dsRNA targets a gene in a lepidopteran, coleopteran, hemipteran or dipteran insect pest, or any combination of the foregoing. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, hemolymph synthesis, hemolymph maintenance, neurotransmission, cell division, energy metabolism, respiration, and apoptosis.

In some embodiments, the polynucleotides of the invention can further comprise, consist essentially of, or consist of a vector. In other embodiments, the polynucleotides and expression cassettes of the invention are comprised within a vector. Vectors for use in transformation of plants and other organisms are well known in the art. Non-limiting examples of general classes of vectors include a plasmid, phage vector, phagemid vector, cosmid vector, fosmid, bacteriophage, artificial chromosome, or a viral vector. In embodiments, the vector is plant vector, e.g., for use in transformation of plants. In embodiments, the vector is a bacterial vector, e.g., for use in transformation of bacteria. Suitable vectors for plants, bacteria and other organisms are known in the art.

The invention also encompasses a transgenic non-human host cell comprising a polynucleotide, a nucleic acid molecule, an expression cassette, a vector, or a polypeptide of the invention. The transgenic non-human host cell can include, but is not limited to, a plant cell (including a monocot cell and/or a dicot cell), a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthro-*

*bacter, Azotobacter, Leuconostoc*, or *Alcaligenes*. Thus, for example, as biological insect control agents, the Txp40 insecticidal proteins of the invention can be produced by expression of a polynucleotide encoding the same in a bacterial cell. For example, in some embodiments, a *Bacillus thuringiensis* cell comprising a polynucleotide encoding a Txp40 insecticidal protein of the invention is provided.

In some embodiments, the transgenic plant cell is a dicot plant cell or a monocot plant cell. In additional embodiments, the dicot plant cell is a soybean cell, sunflower cell, tomato cell, cole crop cell, cotton cell, sugar beet cell or a tobacco cell. In further embodiments, the monocot cell is a barley cell, maize cell, oat cell, rice cell, sorghum cell, sugar cane cell or wheat cell. In embodiments, the invention provides a plurality of dicot cells or monocot cells comprising a polynucleotide expressing a chimeric insecticidal protein of the invention. In other embodiments, the plurality of cells are juxtaposed to form an apoplast and are grown in natural sunlight. In other embodiments, the transgenic plant cell cannot regenerate a whole plant.

In some embodiments of the invention, a Txp40 insecticidal protein of the invention is expressed in a higher organism, for example, a plant. In some embodiments, the plant is infestable by a *Spodoptera* pest, particular infestable by fall armyworm. In other embodiments, the plant infestable by fall armyworm is a corn plant. In this case, transgenic plants expressing effective amounts of the Txp40 insecticidal protein protect themselves from at least *Spodoptera* pests, particularly fall armyworm. When an insect starts feeding on such a transgenic plant, it ingests the expressed Txp40 insecticidal protein. This can deter the insect from further biting into the plant tissue or may even harm or kill the insect. In some embodiments, a polynucleotide of the invention is inserted into an expression cassette, which is then stably integrated in the genome of the plant. In other embodiments, the polynucleotide is included in a non-pathogenic self-replicating virus.

In some embodiments of the invention, a transgenic plant cell comprising a nucleic acid molecule or polypeptide of the invention is a cell of a plant part, a plant organ or a plant culture (each as described herein) including, but not limited to, a root, a leaf, a seed, a flower, a fruit, a pollen cell, organ or plant culture, and the like, or a callus cell or culture.

A transgenic plant or plant cell in accordance with the invention may be a monocot or dicot plant or plant cell and includes, but is not limited to, corn (maize), soybean, rice, wheat, barley, rye, oat, sorghum, millet, sunflower, safflower, sugar beet, cotton, sugarcane, oilseed rape, alfalfa, tobacco, peanut, vegetable (including, sweet potato, bean, pea, chicory, lettuce, cabbage, cauliflower, broccoli, turnip, carrot, eggplant, cucumber, radish, spinach, potato, tomato, asparagus, onion, garlic, melon, pepper, celery, squash, pumpkin, zucchini, and the like), fruit (including, apple, pear, quince, plum, cherry, peach, nectarine, apricot, strawberry, grape, raspberry, blackberry, pineapple, avocado, papaya, mango, banana, and the like), a specialty plant or plant cell (such as *Arabidopsis*), or a woody plant or plant cell (such as coniferous and/or deciduous trees). In embodiments, a plant or plant cell of the of the invention is a crop plant or plant cell such as maize, sorghum, wheat, sunflower, tomato, a crucifer, pepper, potato, cotton, rice, soybean, sugar beet, sugarcane, tobacco, barley, oilseed rape plant or plant cell, and the like.

The invention further provides a part of a transgenic plant of the invention. Optionally, the plant part comprises a chimeric insecticidal protein of the invention and/or a nucleic acid encoding the same.

The invention further provides a seed of a transgenic plant of the invention or a seed that produces the transgenic plant of the invention. Optionally, the seed comprises a chimeric insecticidal protein of the invention and/or a nucleic acid encoding the same.

Additional embodiments of the invention include harvested products produced from the transgenic plants, plant parts or seed of the invention, as well as a processed product produced from a harvested product. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention. Optionally, the harvested product or the processed product comprises a chimeric insecticidal protein of the invention and/or a nucleic acid encoding the same.

In other embodiments, the invention provides an extract from a transgenic plant, plant part or of the invention, optionally wherein the extract comprises a chimeric insecticidal protein of the invention and/or a nucleic acid encoding the same. Extracts from plants or plant parts can be made according to procedures well known in the art (See, de la Torre et al., Food, Agric. Environ. 2(1):84-89 (2004); Guidet, Nucleic Acids Res. 22(9): 1772-1773 (1994); Lipton et al., Food Agric. Immun. 12:153-164 (2000)).

The chimeric insecticidal protein can function in the plant part, plant cell, plant organ, seed, harvested product, processed product or extract, and the like, as an insect control agent. In other words, the chimeric insecticidal protein can continue to perform the insecticidal function it had in the transgenic plant. The nucleic acid can function to express the chimeric insecticidal protein. As an alternative to encoding the insecticidal protein of the invention, the nucleic acid can function to identify a transgenic plant part, plant cell, plant organ, seed, harvested product, processed product or extract of the invention.

In embodiments, a transgenic plant, plant part, plant cell, plant organ, or seed of the invention is hemizygous for a polynucleotide or expression cassette of the invention. In embodiments, a transgenic plant, plant part, plant cell, plant organ, or seed of the invention is homozygous for a polynucleotide or expression cassette of the invention.

In embodiments, a transgenic plant, plant part, plant cell, plant organ, seed, harvested product, processed product or extract has increased resistance to one or more insect pests (e.g., a lepidopteran pest, such as fall armyworm) as compared with a suitable control that does not comprise a nucleic acid encoding an insecticidal protein of the invention.

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (Cell. Mol. Biol. Lett. 7:849-858 (2002)).

For *Agrobacterium*-mediated transformation, binary vectors or vectors carrying at least one T-DNA border sequence are generally suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., Biotechnology 4:1093-1096 (1986)). For both direct gene transfer and *Agrobacterium*-mediated transfer, transformation is usually (but not necessarily) undertaken with a selectable marker that may be a positive selection (e.g., Phosphomannose Isomerase), provide resistance to an antibiotic (e.g., kanamycin, hygromycin or methotrexate) or a herbicide (e.g., glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Höfgen & Willmitzer (1988) Nucleic Acids Res. 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an Agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) Proc. Nati. Acad. Sci. USA 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) Proc. Natl. Acad. Sci. USA 87, 8526-8530; Staub, J. M., and Maliga, P. (1992) Plant Cell 4, 39-45). The presence of cloning sites between these markers allows creation of a plastid targeting vector for introduction of foreign genes (Staub, J. M., and Maliga, P. (1993) EMBO J. 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) Proc. Natl. Acad. Sci. USA 90, 913-917). Previously, this marker had been used successfully for high-frequency transformation of the plastid genome of the green alga *Chlamydomonas reinhardtii* (Goldschmidt-Clermont, M. (1991) Nucl. Acids Res. 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10 of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Once a desired polynucleotide has been transformed into a particular plant species, it may be propagated in that species or moved into other varieties of the same species, particularly including commercial varieties, using traditional breeding techniques.

In some embodiments, the invention provides an insecticidal composition comprising a chimeric insecticidal protein of the invention in an agriculturally acceptable carrier. As used herein an "agriculturally-acceptable carrier" can include natural or synthetic, organic or inorganic material which is combined with the active protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing an insecticidal protein of the invention in planta is an agriculturally-acceptable carrier of the expressed insecticidal protein. In embodiments, the compositions and agriculturally-acceptable carriers of the invention exclude transgenic plants.

In further embodiments, the insecticidal composition comprises a bacterial cell or a transgenic bacterial cell of the invention, wherein the bacterial cell or transgenic bacterial cell produces an insecticidal protein of the invention. Such an insecticidal composition can be prepared by desiccation, lyophilization, homogenization, extraction, filtration, centrifugation, sedimentation, or concentration of a culture of *Bacillus thuringiensis* (Bt), including a transgenic Bt culture. In embodiments, a composition of the invention may comprise at least about 1, at least about 5, at least about 10, at least about 20, at least about 25, at least about 30, at least about 35, at least about 40, at least about 50, at least about 60, at least about 70, at least about 80, at least about 90, at least about 95, at least about 97, or at least 99 by weight a polypeptide of the invention. In additional embodiments, the composition comprises from about 1 to about 99 by weight of the insecticidal protein of the invention.

The insecticidal proteins of the invention can be used in combination with other pest control agents to increase pest target spectrum and/or for the prevention or management of insect resistance. Furthermore, the use of the insecticidal proteins of the invention in combination with an insecticidal agent which has a different mode of action or target a different receptor in the insect gut has particular utility for the prevention and/or management of insect resistance.

Therefore, in some embodiments, the invention provides a composition that controls one or more plant pests (e.g., an insect pest such as a lepidopteran insect pest, a coleopteran insect pest, a hemipteran insect pest and/or a dipteran insect pest), wherein the composition comprises a first pest control agent, which is a chimeric insecticidal protein of the invention and at least a second pest control agent that is different from the first pest control agent. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first pest control agent, which is a chimeric insecticidal protein of the invention when the transgenic plant comprises the second pest control agent. In other embodiments, the formulation comprises the second pest control agent when the transgenic plant comprises the first pest control agent, which is a chimeric insecticidal protein of the invention.

In some embodiments, the second pest control agent can be one or more of a chemical pesticide, such as an insecticide, a *Bacillus thuringiensis* (Bt) insecticidal protein, and/or a non-Bt pesticidal agent including without limitation a

*Xenorhabdus* insecticidal protein, a *Photorhabdus* insecticidal protein, a *Brevibacillus laterosporus* insecticidal protein, a *Bacillus sphaericus* insecticidal protein, a protease inhibitor (both serine and cysteine types), a lectin, an alpha-amylase, a peroxidase, a cholesterol oxidase, or a double stranded RNA (dsRNA) molecule.

In other embodiments, the second pest control agent is one or more chemical pesticides, which is optionally a seed coating. Non-limiting examples of chemical pesticides include pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is one or more of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from one or more of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from: Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1 Da, Cry1db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa, Cry73Aa, or any combination of the foregoing. In embodiments, the Cry protein is a Cry1Fa, for example, as represented by maize event TC1507.

In further embodiments, the second pest control agent is one or more Vip3 vegetative insecticidal proteins selected from Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa2, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag1, Vip3Ag2, Vip3Ag3 HM117633, Vip3Ag4, Vip3Ag5, Vip3Ah1, Vip3Ba1, Vip3Ba2, Vip3Bb1, Vip3Bb2, Vip3Bb3, or any combination of the foregoing. In embodiments, the Vip3 protein is Vip3Aa (U.S. Pat. No. 6,137,033), for example, as represented by corn event MIR162 (U.S. Pat. Nos. 8,232,456; 8,455,720; and 8,618,272).

In embodiments, the second pest control agent may be derived from sources other than *B. thuringiensis*. For example, the second pest control agent can be an alpha-amylase, a peroxidase, a cholesterol oxidase, a patatin, a protease, a protease inhibitor, a urease, an alpha-amylase inhibitor, a pore-forming protein, a chitinase, a lectin, an engineered antibody or antibody fragment, a *Bacillus cereus* insecticidal protein, a *Xenorhabdus* spp. (such as *X. nematophila* or *X. bovienii*) insecticidal protein, a *Photorhabdus* spp. (such as *P. luminescens* or *P. asymobiotica*) insecticidal protein, a *Brevibacillus* spp. (such as *B. laterosporous*) insecticidal protein, a *Lysinibacillus* spp. (such as *L. sphearicus*) insecticidal protein, a *Chromobacterium* spp. (such as *C. subtsugae* or *C. piscinae*) insecticidal protein, a *Yersinia* spp. (such as *Y. entomophaga*) insecticidal protein, a *Paenibacillus* spp. (such as *P. propylaea*) insecticidal protein, a *Clostridium* spp. (such as *C. bifermentans*) insecticidal protein, a *Pseudomonas* spp. (such as *P. fluorescens*) and a lignin. In other embodiments, the second agent may be at least one insecticidal protein derived from an insecticidal toxin complex (Tc) from *Photorhabdus, Xenorhabus, Serratia*, or *Yersinia*. In other embodiments. The insecticidal protein may be an ADP-ribosyltransferase derived from an insecticidal bacteria, such as *Photorhabdus* ssp. In other embodiments, the insecticidal protein may be a VIP protein, such as VIP1 and/or VIP2 from *B. cereus*. In still other embodiments, the insecticidal protein may be a binary toxin derived from an insecticidal bacteria, such as ISP1A and ISP2A from *B. laterosporous* or BinA and BinB from *L. sphaericus*. In still other embodiments, the insecticidal protein may be engineered or may be a hybrid or chimera of any of the preceding insecticidal proteins.

In some embodiments, the second pesticidal agent can be non-proteinaceous, for example, an interfering RNA molecule such as a dsRNA, which can be expressed transgenically or applied as part of a composition (e.g., using topical methods). An interfering RNA typically comprises at least a RNA fragment against a target gene, a spacer sequence, and a second RNA fragment which is complementary to the first, so that a double-stranded RNA structure can be formed. RNA interference (RNAi) occurs when an organism recognizes double-stranded RNA (dsRNA) molecules and hydrolyzes them. The resulting hydrolysis products are small RNA fragments of about 19-24 nucleotides in length, called small interfering RNAs (siRNAs). The siRNAs then diffuse or are carried throughout the organism, including across cellular membranes, where they hybridize to mRNAs (or other RNAs) and cause hydrolysis of the RNA. Interfering RNAs are recognized by the RNA interference silencing complex (RISC) into which an effector strand (or "guide strand") of the RNA is loaded. This guide strand acts as a template for the recognition and destruction of the duplex sequences. This process is repeated each time the siRNA hybridizes to its complementary-RNA target, effectively preventing those mRNAs from being translated, and thus "silencing" the expression of specific genes from which the mRNAs were transcribed. Interfering RNAs are known in the art to be useful for insect control (see, for example, publication WO2013/192256, incorporated by reference herein). An interfering RNA designed for use in insect control produces a non-naturally occurring double-stranded RNA, which takes advantage of the native RNAi pathways in the insect to trigger down-regulation of target genes that may lead to the cessation of feeding and/or growth and may result in the death of the insect pest. The interfering RNA molecule may confer insect resistance against the same target pest as the protein of the invention or may target a different pest. The targeted insect plant pest may feed by chewing, sucking, or piercing. Interfering RNAs are known in the art to be useful for insect control. In embodiments, the dsRNA useful for insect control is described in U.S. Provisional Application Nos. 62/371,259, 62/371,261, or 62/371,262, filed on Aug. 5, 2016. In embodiments, the dsRNA useful for insect control is described in U.S. Pat. Nos. 9,238,8223, 9,340,797, or 8,946,510. In embodiments, the dsRNA useful for insect control is described in U.S. patent application Ser. Nos. 12/868,994, 13/831,230, 14/207,313, or 14/207,318. In other embodiments, the interfering RNA may confer resistance against a non-insect plant pest, such as a nematode pest or a virus pest.

In still further embodiments, the first insect control agent, which is a chimeric insecticidal protein of the invention and the second pest control agent are co-expressed in a transgenic plant. This co-expression of more than one pesticidal principle in the same transgenic plant can be achieved by genetically engineering a plant to contain and express the nucleic acid sequences encoding the insect control agents. For example, the co-expression of more than one pesticidal agent in the same transgenic plant can be achieved by making a single recombinant vector comprising coding sequences of more than one pesticidal agent in a "molecular stack" and genetically engineering a plant to contain and express all the pesticidal agents in the transgenic plant. Such molecular stacks may be also be made by using mini-chromosomes as described, for example in U.S. Pat. No. 7,235,716. Alternatively, a plant, Parent 1, can be genetically engineered for the expression of the chimeric insecticidal protein of the invention. A second plant, Parent 2, can be genetically engineered for the expression of a second pest control agent. By crossing Parent 1 with Parent 2, progeny plants are obtained which express both insect control agents from Parents 1 and 2.

In other embodiments, the invention provides a stacked transgenic plant resistant to plant pest infestation comprising a nucleic acid (e.g., DNA) sequence encoding a dsRNA for suppression of an essential gene in a target pest and a nucleic acid e.g., (DNA) sequence encoding a chimeric insecticidal protein of the invention exhibiting insecticidal activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, a chimeric insecticidal protein of the invention acts to transiently reduce the midgut pH which serves to stabilize the co-ingested dsRNA rendering the dsRNA effective in silencing the target genes.

Transgenic plants or seed comprising and/or expressing an insecticidal protein of the invention can also be treated with an insecticide or insecticidal seed coating as described in U.S. Pat. Nos. 5,849,320 and 5,876,739. In embodiments, where both the insecticide or insecticidal seed coating and the transgenic plant or seed of the invention are active against the same target insect, for example a lepidopteran pest (e.g., fall armyworm), the combination is useful (i) in a method for further enhancing activity of the composition of the invention against the target insect, and/or (ii) in a method for preventing development of resistance to the composition of the invention by providing yet another mechanism of action against the target insect. Thus, in embodiments, the invention provides a method of enhancing control of a lepidopteran insect population comprising providing a transgenic plant or seed of the invention and applying to the plant or the seed an insecticide or insecticidal seed coating to a transgenic plant or seed of the invention.

Even where the insecticide or insecticidal seed coating is active against a different insect, the insecticide or insecticidal seed coating is useful to expand the range of insect control, for example by adding an insecticide or insecticidal seed coating that has activity against coleopteran insects to a transgenic seed of the invention, which, in some embodiments, has activity against lepidopteran insects, the coated transgenic seed produced controls both lepidopteran and coleopteran insect pests.

The invention also encompasses methods of producing an insect-resistant (e.g., a lepidopteran insect-resistant) transgenic plant. In representative embodiments, the method comprises: introducing into a plant a polynucleotide, expression cassette or vector of the invention comprising a nucleotide sequence that encodes a chimeric insecticidal protein of the invention (including toxin fragments and modified forms that are substantially identical to the polypeptides specifically disclosed herein), wherein the nucleotide sequence is expressed in the plant to produce the chimeric insecticidal protein of the invention, thereby conferring to the plant resistance to the insect pest, and producing an insect-resistant transgenic plant (e.g., as compared with a suitable control plant, such as a plant that does not comprise the polynucleotide, expression cassette or vector of the invention and/or does not express a polypeptide of the invention).

In embodiments, the method of introducing the polynucleotide, expression cassette or vector of the invention into the plant comprises first transforming a plant cell with the polynucleotide, expression cassette or vector and regenerating a transgenic plant therefrom, where the transgenic plant comprises the polynucleotide, expression cassette or vector and expresses the chimeric insecticidal protein of the invention.

Alternatively, or additionally, the introducing step can comprise crossing a first plant comprising the polynucleotide, expression cassette or vector with a second plant (e.g., a different plant from the first plant, for example, a plant that does not comprise the polynucleotide, expression cassette or vector) and, optionally, producing a progeny plant that comprises the polynucleotide, expression cassette or vector and expresses a chimeric insecticidal protein of the invention, thereby resulting in increased resistance to at least one insect pest. Thus, a transgenic plant of the invention encompasses a plant that is the direct result of a transformation event and the progeny thereof (of any generation) that comprise the polynucleotide, expression cassette or vector and optionally expresses the chimeric insecticidal protein resulting in increased resistance to at least one insect pest.

The invention further provides a method of identifying a transgenic plant of the invention, the method comprising detecting the presence of a polynucleotide, expression cassette, vector or chimeric insecticidal protein of the invention in a plant (or a plant cell, plant part, and the like derived therefrom), and thereby identifying the plant as a transgenic plant of the invention based on the presence of the polynucleotide, expression cassette, vector or chimeric insecticidal protein of the invention.

The invention further provides a method of producing a transgenic plant with increased resistance to at least one insect pest (e.g., a least one lepidopteran pest), the method comprising: planting a seed comprising a polynucleotide, expression cassette or vector of the invention, and growing a transgenic plant from the seed, where the transgenic plant comprises the polynucleotide, expression cassette or vector and produces the chimeric insecticidal protein.

In embodiments, transgenic plants produced by the methods of the invention comprise a polynucleotide, expression cassette or vector of the invention. In embodiments, a transgenic plant produced by the methods of the invention comprise a chimeric insecticidal protein of the invention and, optionally have increased resistance to at least one insect pest.

The methods of producing a transgenic plant described herein optionally comprise a further step of harvesting a seed from the transgenic plant, where the seed comprises the polynucleotide, expression cassette or vector and produces the chimeric insecticidal protein. Optionally, the seed produces a further transgenic plant that comprises the polynucleotide, expression cassette or vector and produces the chimeric insecticidal protein, and thereby has increased resistance to at least one insect pest.

The invention further provides plant parts, plant cells, plant organs, plant cultures, seed, plant extracts, harvested products and processed products of the transgenic plants produced by the methods of the invention.

As a further aspect, the invention also provides a method of producing seed, the method comprising: providing a transgenic plant that comprises a polynucleotide, expression cassette or vector of the invention, and harvesting a seed from the transgenic plant, wherein the seed comprises the polynucleotide, expression cassette, vector and produces the chimeric insecticidal protein. Optionally, the seed produces a further transgenic plant that comprises the polynucleotide, expression cassette or vector and produces the chimeric insecticidal protein, and thereby has increased resistance to at least one insect pest. In representative embodiments, the step of providing the transgenic plant comprises planting a seed that produces the transgenic plant.

The invention further provides a method of producing a hybrid plant seed, the method comprising: crossing a first inbred plant, which is a transgenic plant comprising a polynucleotide, expression cassette or vector of the invention, and optionally expressing a chimeric insecticidal protein of the invention with a different inbred plant (e.g., an inbred plant that does not comprise a polynucleotide, expression cassette or vector of the invention) and allowing hybrid seed to form. Optionally, the method further comprises harvesting a hybrid seed. In embodiments, the hybrid seed comprises the polynucleotide, expression cassette or vector of the invention, and in embodiments may further comprise a chimeric insecticidal protein of the invention and have increased resistance to an insect pest. In embodiments, the hybrid seed produces a transgenic plant that comprises the polynucleotide, expression cassette or vector of the invention, expresses the chimeric insecticidal protein of the invention, and has increased resistance to at least one insect pest.

In some embodiments, a transgenic plant of the invention is resistant to at least one lepidopteran insect pest (as described herein). In embodiments, the transgenic plant controls a fall armyworm insect pest or colony that is resistant to a Vip3A (e.g., a Vip3Aa protein, for example, as expressed in maize event MIR162) and/or Cry1F protein (e.g., a Cry1Fa protein, for example, as expressed in maize event TC1507).

In further embodiments, a method of controlling at least one insect pest (e.g., at least one lepidopteran insect pest, such as fall armyworm) comprises providing a chimeric insecticidal protein of the invention. In embodiments, the method comprises delivering (e.g., orally delivering) to the insect pest or an environment thereof an effective amount of a chimeric insecticidal protein of the invention. Generally, to be effective, the polypeptide is orally ingested by the insect. However, the chimeric insecticidal protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition (s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic proteins of the invention. In some particular embodiments, the chimeric insecticidal protein of the invention is delivered orally to an insect, for example, where the insect ingests one or more parts of a transgenic plant of the invention.

In other embodiments, the insecticidal protein of the invention is delivered orally to an insect, wherein the insect ingests one or more parts of a plant sprayed with a composition comprising the insecticidal protein of the invention. Delivering the composition of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with a compound(s), composition(s) or formulation(s) are well-known to those of skill in the art.

In some embodiments, the invention encompasses a method of providing a farmer with a means of controlling a *Spodoptera* pest insect, the method comprising supplying or selling to the farmer plant material such as a seed, the plant material comprising a Txp40 polynucleotide, expression cassette or vector capable of expressing a Txp40 insecticidal protein of the invention. In other embodiments, the *Spodoptera* insect pest is a fall armyworm pest and the plant material comprises the Txp40 insecticidal protein of the invention and, optionally, has increased resistance to at least fall armyworm. In other embodiments, the plant material is a corn seed, and a corn plant grown from the seed comprises the Txp40 polynucleotide, expression cassette or vector of the invention, that expresses a Txp40 insecticidal protein of the invention, and has increased resistance to the at least fall armyworm.

EXAMPLES

The invention will be further described by reference to the following detailed examples. These examples are provided for the purposes of illustration only, and are not intended to be limiting unless otherwise specified. Standard recombinant DNA and molecular cloning techniques used here are well known in the art and are described by J. Sambrook, et al., *Molecular Cloning: A Laboratory Manual, 3d Ed.*, Cold Spring Harbor, NY: Cold Spring Harbor Laboratory Press (2001); by T. J. Silhavy, M. L. Berman, and L. W. Enquist, *Experiments with Gene Fusions*, Cold Spring Harbor Laboratory, Cold Spring Harbor, NY (1984) and by Ausubel, F. M. et al., *Current Protocols in Molecular Biology*, New York, John Wiley and Sons Inc., (1988), Reiter, et al., *Methods in Arabidopsis Research*, World Scientific Press (1992), and Schultz et al., *Plant Molecular Biology Manual*, Kluwer Academic Publishers (1998).

Example 1. Insecticidal Activity of Txp40 Protein Against Cry Resistant Fall Armyworm Insecticidal activity of a Txp40 protein (SEQ ID NO:1), obtained from *Photorhabdus lumimescens*, was determined using an artificial diet bioassay in which an *E. coli* extract comprising a Txp40 protein was overlaid on the surface of artificial insect diet. The strain of FAW that was used in these bioassays is derived from a field population of FAW that is resistant to the Cry1F and the Cry1Ab insecticidal proteins. A Vip3 protein was used as the positive control. An *E. coli* clone comprising an empty vector, i.e. a vector without a txp40 coding sequence, was used as a negative control. Results of the bioassays are recorded as percent mortality and effective mortality on day 7, where effective mortality considers the growth stage attained by the FAW larvae during the test, i.e. treated larvae that have growth inhibition and are moribund are counted as effectively dead.

The results are shown in Table 1. When *E. coli* extracts comprising Txp40 were tested in the insect bioassay, the Txp40 surprisingly showed significant insecticidal activity against Cry1F-resistant FAW. These results not only demonstrate the surprising oral activity of Txp40 protein against FAW, but also show that Txp40 has a different mode of action than the Cry1F and Cry1Ab insecticidal proteins from *B. thuringiensis*.

TABLE 1

Insecticidal activity of Txp40 against Cry resistant fall armyworm.

| Treatment | Mortality | Instar L1 | L2 | L3 | Effective mort. |
|---|---|---|---|---|---|
| BL21*/pET29a-empty, pH 7 | 17 | 0 | 0 | 10 | 17 |
| BL21*/pET29a-empty, pH 10.5 | 0 | 1 | 1 | 10 | 8 |
| BL21*/Photo_lumin_txp40, pH 7 | 83 | 1 | 1 | 0 | 92 |
| BL21*/Vip3D, pH 10.5 | 67 | 4 | 0 | 0 | 100 |

To test the potency of Txp40 protein, dilutions of the Txp40 *E. coli* extracts were made and added to the surface of artificial insect diet as described above. Undiluted extracts were also tested for both the Txp40 treatment as well as the Vip3 positive control treatment.

Results, shown in Table 2. demonstrate that the Txp40 protein has significant activity even at a 1:32 dilution, which indicates that expression of Txp40 in transgenic corn plants would be a viable FAW control option, particularly for Cry-resistant FAW.

TABLE 2

Potency of Txp40-1 against Cry-resistant FAW.

| Treatment | Mortality | Instar L1 | L2 | L3 | Effective mort. |
|---|---|---|---|---|---|
| BL21*/pET29a-empty, pH 8.5 | 8 | 0 | 0 | 11 | 8 |
| BL21*/Photo_lumin_txp40, pH 8.5 | 100 | 0 | 0 | 0 | 100 |
| BL21*/Photo_lumin_txp40 1:2, pH 8.5 | 83 | 2 | 0 | 0 | 100 |
| BL21*/Photo_lumin_txp40 1:4, pH 8.5 | 67 | 2 | 2 | 0 | 83 |
| BL21*/Photo_lumin_txp40 1:8, pH 8.5 | 67 | 4 | 0 | 0 | 100 |

TABLE 2-continued

| Potency of Txp40-1 against Cry-resistant FAW. | | | | | |
|---|---|---|---|---|---|
| | | Instar | | | Effective |
| Treatment | Mortality | L1 | L2 | L3 | mort. |
| BL21*/Photo_lumin_txp40 1:16, pH 8.5 | 67 | 2 | 1 | 1 | 83 |
| BL21*/Photo_lumin_txp40 1:32, pH 8.5 | 58 | 1 | 4 | 0 | 67 |
| BL21*/pET29a-empty, pH 10.5 | 0 | 2 | 2 | 8 | 17 |
| BL21*/Vip3D, pH 10.5 | 83 | 2 | 0 | 0 | 100 |
| BL21*/Vip3D 1:2, pH 10.5 | 42 | 7 | 0 | 0 | 100 |
| BL21*/Vip3D 1:4, pH 10.5 | 92 | 1 | 0 | 0 | 100 |
| BL21*/Vip3D 1:8, pH 10.5 | 75 | 3 | 0 | 0 | 100 |
| BL21*/Vip3D 1:16, pH 10.5 | 92 | 1 | 0 | 0 | 100 |
| BL21*/Vip3D 1:32, pH 10.5 | 67 | 4 | 0 | 0 | 100 |

Example 2. FAW Activity of Txp40 Variants

Mutations were introduced in Txp40-1 (SEQ ID NO: 1) and the protein stability and insecticidal activity of bacterial lysates from each Txp40) variant were assayed. Mutations included amino acid changes at various residues and also the insertion and/or deletion of amino acid residues. Variant Txp40 proteins having one or more mutations were tested for insecticidal activity against two strains of fall armywormn, a strain from Brazil (BR-FAW; *Spodoptera frugiperda*) and a strain from North America (NA-FAW; *Spodoptera frugiperda*) using diet-overlay assays performed essentially as described in Example 1. A vegetative insecticidal protein, Vip3D, the wild-type Txp40 protein and/or a *Bacillus thuringiensis* strain C0756, were used as positive controls. pET29 empty vector was used as a negative control. Tables 3-4 show the results for expression, solubility and/or insecticidal activity assays of variant Txp40 proteins with targeted mutations.

TABLE 3

| Activity of variant Txp40 proteins with single mutations. | | | | |
|---|---|---|---|---|
| | | | Effective % Mortality | |
| Txp40 Variant (SEQ ID NO:) [Amino Acid Substitution] | Expression | Solubility | NA-FAW | BR-FAW |
| K31A (SEQ ID NO: 74) | High | High | 81 | 67 |
| K48A (SEQ ID NO: 75) | High | High | 38 | 42 |
| K49A (SEQ ID NO: 76) | High | High | 75 | 58 |
| K73A (SEQ ID NO: 77) | High | High | 50 | 75 |
| K75A (SEQ ID NO: 78) | High | High | 69 | 42 |
| K103A (SEQ ID NO: 79) | High | High | 56 | 75 |
| K111A (SEQ ID NO: 80) | High | High | 69 | 17 |
| K119A (SEQ ID NO: 81) | High | High | 69 | 50 |
| K133A (SEQ ID NO: 82) | High | High | 19 | 8 |
| K143A (SEQ ID NO: 83) | Med | Low | 6 | 8 |
| K170A (SEQ ID NO: 84) | High | High | 62 | 50 |
| K191A (SEQ ID NO: 85) | High | High | 50 | 46 |
| K200A (SEQ ID NO: 86) | High | High | 69 | 58 |
| K209A (SEQ ID NO: 87) | High | High | 50 | 8 |
| K210A (SEQ ID NO: 88) | High | High | 56 | 42 |
| K213A (SEQ ID NO: 89) | High | High | 62 | 75 |
| K221A (SEQ ID NO: 90) | High | High | 62 | 67 |
| K238A (SEQ ID NO: 91) | High | High | 50 | 27 |
| K247A (SEQ ID NO: 92) | High | High | 31 | 50 |
| K250A (SEQ ID NO: 93) | High | High | 43 | 42 |
| K263A (SEQ ID NO: 94) | High | High | 0 | 0 |
| K265A (SEQ ID NO: 95) | High | High | 6 | 0 |
| K271A (SEQ ID NO: 96) | High | High | 0 | 25 |
| K275A (SEQ ID NO: 97) | High | High | 25 | 17 |
| K284A (SEQ ID NO: 98) | High | High | 56 | 75 |
| K296A (SEQ ID NO: 99) | High | High | 12 | 8 |
| K309A (SEQ ID NO: 100) | High | High | 50 | 50 |
| K333A (SEQ ID NO: 101) | High | High | 81 | 42 |
| R10A (SEQ ID NO: 102) | High | High | 50 | 33 |
| R26A (SEQ ID NO: 103) | High | High | 44 | 67 |
| R46A (SEQ ID NO: 104) | High | High | 44 | 50 |
| R167A (SEQ ID NO: 105) | High | High | 62 | 67 |
| R186A (SEQ ID NO: 106) | High | High | 50 | 42 |
| R187A (SEQ ID NO: 107) | High | Med | 12 | 42 |
| R208A (SEQ ID NO: 108) | High | High | 75 | 58 |
| R217A (SEQ ID NO: 109) | High | Med | 12 | 58 |
| R226A (SEQ ID NO: 110) | High | High | 50 | 8 |
| R240A (SEQ ID NO: 111) | High | High | 6 | 33 |
| R252A (SEQ ID NO: 112) | High | High | 56 | 50 |
| R305A (SEQ ID NO: 113) | High | High | 6 | 0 |
| R311A (SEQ ID NO: 114) | High | High | 0 | 0 |
| Txp40 WT (SEQ ID NO: 1) | High | High | 46 | 61 |
| pET29a-empty | ND | ND | 0 | 0 |
| Vip3D | High | High | 100 | 100 |

TABLE 4

| Activity of variant Txp40 proteins with multiple mutations. | | | |
|---|---|---|---|
| Txp40 Variant (SEQ ID NO:) [Amino Acid Substitutions] | Expression | Solubility | NA-FAW % mortality |
| K31A/K49A (SEQ ID NO: 115) | High | High | 0 |
| K31A/K333A (SEQ ID NO: 116) | High | High | 6 |
| K31A/R208A (SEQ ID NO: 117) | High | High | 44 |
| R208A/K333A (SEQ ID NO: 118) | High | High | 25 |
| K49A/R208A (SEQ ID NO: 119) | High | High | 31 |
| K49A/K333A (SEQ ID NO: 120) | High | High | 0 |
| K31A/K49A/K333A (SEQ ID NO: 121) | High | High | 0 |
| K31A/K49A/R208A/K333A (SEQ ID NO: 122) | High | High | 0 |
| K73A/K213A (SEQ ID NO: 123) | High | High | 38 |
| K103A/K213A (SEQ ID NO: 124) | High | High | 38 |
| K213A/K284A (SEQ ID NO: 125) | High | High | 56 |
| K31A/K49A/K213A (SEQ ID NO: 126) | High | High | 6 |
| K119A/K213A (SEQ ID NO: 127) | High | High | 88 |
| K213A/R167A (SEQ ID NO: 128) | High | High | 38 |
| K119A/R167A (SEQ ID NO: 129) | High | High | 50 |
| pET29a-empty | ND | ND | 0 |

Results in Table 3 demonstrate that variant Txp40 proteins can be produced that have equal or better insecticidal activity to fall armyworm (FAW) compared to the wild-type Txp40 protein. For example, variant proteins with single mutations at K73A, K191A, K209A. K238A, K309A, R10A, R26A, R46A, R186A and R226A had approximately the same insecticidal activity as wild-type Txp40 against NA-FAW, and K49A, K200A, K221A, R26A, R167A, R208A and R217A had approximately the same insecticidal activity as wild-type Txp40 against BR-FAW.

Certain of the mutations in Txp40 created variant proteins that had increased or significantly increased (1-20%) insecticidal activity against NA-FAW compared to the wild-type Txp40 protein. For example, variant proteins with single mutations at K31A, K49A, K73A, K75A, K103A, K111A, K119A, K170A, K191A, K200A, K210A, K213A, K221A, K284A, K333A. R167A, R208A, and R252A all had better activity against NA-FAW compared to the wild-type Txp40 and of those mutants, K31A, K49A, K75A, K111A, K119A, K200A and K333A had 20% or greater increase in insecticidal activity to NA-FAW compared to wild-type Txp40. Certain of the mutations in Txp40 created variant proteins that had increased or significantly increased (≥14%) insecticidal activity against BR-FAW compared to the wild-type Txp40 protein. For example, variant proteins with single mutations at K31A, K49A, K73A, K75A, K103A, K111A, K119A, K200A, K213A and K333A all had better activity against BR-FAW compared to the wild-type Txp40 and of those K73A, K103A and K213A had significantly increased insecticidal activity against BR-FAW compared to wild-type Txp40 protein.

Results further demonstrate that certain mutations in Txp40 (SEQ ID NO:1) created variant proteins that were surprisingly differentially toxic to NA-FAW compared to BR-FAW. Some mutants were more toxic to NA-FAW than BR-FAW, for example K31A, K48A, K75A, K111A, K119A, K133A, K170A, K209A, K210A, K238A, K333A, R10A, R208A and R226A. Some variants were more toxic to BR-FAW than NA-FAW, for example, K73A, K103A, K213A, K247A, K271A, K284A, R26A, R46A, R187A, R217A, and R240A, indicating that these positions are important for differential FAW activity.

Most of the variant Txp40 proteins comprising multiple mutations had reduced insecticidal activity against NA-FAW compared to the wild-type Txp40 and some mutations knocked out activity completely, again indicating the importance of these amino acid positions to the biological activity of Txp40. Some of the variants with multiple mutations had equal activity to the wild-type Txp40 and one variant with mutations at positions K119A/K213A (SEQ ID NO: 127) increased the insecticidal activity significantly compared to wild-type Txp40.

DNA encoding the variant Txp40-K119A/K213A protein (SEQ ID NO:127) was used as a template to produce further mutations using a degenerated oligonucleotide random mutagenesis technique on the full-length Txp40-K119A/K213A DNA carried out by GenScript® (Piscataway, NJ). A library of variants comprising the random mutations was subcloned into a pET29a vector. Hundreds of bacterial lysates comprising a variant Txp40 protein were tested for insecticidal activity against NA-FAW, BR-FAW and soybean looper (SBL; *Chrysodeixis includens*) as described above. Results for certain variants are shown in Table 5.

TABLE 5

Activity of variant Txp40 proteins comprising random mutations.

| Txp40 Variant (SEQ ID NO:) [Amino Acid Substitutions] | Effective % Mortality NA-FAW | BR-FAW | SBL |
|---|---|---|---|
| K119A/K213A (SEQ ID NO: 127) Template | 97 | 64 | 50 |
| K119A/K213A/S11Y (SEQ ID NO: 131) | 100 | 92 | 83 |
| K119A/S11Y/M86I/K213T (SEQ ID NO: 130) | 92 | 83 | 50 |
| K119A/K213A/F169V (SEQ ID NO: 132) | 92 | 75 | 50 |
| K119A/K213A/P134L (SEQ ID NO: 133) | 75 | 83 | 58 |
| K119A/K213A/I101L/K103T/N257T (SEQ ID NO: 134) | 75 | 50 | 50 |
| K119A/K213A/H62Q/D99V/T165I/R167C (SEQ ID NO: 135) | 92 | 50 | 67 |
| K119A/K213A/L316V (SEQ ID NO: 136) | 92 | 42 | 58 |
| BtC0756 (+) | 100 | 100 | 100 |
| pET29a-empty | 0 | 17 | 0 |

As described above, wild-type Txp40 (SEQ ID NO:1) and the variant Txp40 proteins have differential toxicity to NA-FAW and BR-FAW. The objective of the randomization experiment was to identify one or more Txp40 variants comprising mutations that conferred high insecticidal activity against both NA- and BR-FAW strains as well as other lepidopteran species. The Txp40 variant comprising the K119A/K213A mutations (SEQ ID NO: 127), that was used as the template for random mutagenesis is very active against NA-FAW but has much lower activity against BR-FAW and SBL (See Table 5).

Results of bioassays of hundreds of the randomly mutagenized Txp40 mutants indicated that a large majority maintained differential toxicity to NA-FAW and BR-FAW. However, three variants, Txp40-K119A/K213A/S11Y/M86I (SEQ ID NO:130); Txp40-K119A/K213A/S11Y (SEQ ID NO:131) and Txp40-K119A/K213A/F169V (SEQ ID NO:132), were identified that maintained the high activity against NA-FAW and surprisingly also had very high activity against BR-FAW compared to the activity of the wild-type Txp40 (SEQ ID NO:1) and the Txp40-K119A/K213A variant (SEQ ID NO:127) that was used as the template. One of those variant, Txp40-K119A/K213A/S11Y (SEQ ID NO:131) also surprisingly had significantly increased activity against soybean looper (SBL) compared to the variant template, Txp40-K119A/K213A. These results strongly suggest that amino acid positions 11, 119 and 213 of SEQ ID NO:1 are very important in determining the insecticidal efficacy of the Txp40 protein.

Still other variant Txp40 proteins that were made and tested against NA-FAW as described above are shown in Table 6. All mutations in Table 6 refer to amino acid substitutions in SEQ ID NO:1.

TABLE 6

Activity of variant Txp40 proteins comprising mutations in SEQ ID NO: 1.

| Txp40 Variant Amino Acid Substitutions in SEQ ID NO: 1 | NA-FAW % mortality | Txp40 Mutant Amino Acid Substitutions in SEQ ID NO: 1 | NA-FAW % mortality |
|---|---|---|---|
| K119A/K213A/H62Q | 44 | K75Q/N126K | 50 |
| K119T/K213T | 75 | S139G/R167H/F169Y/R208H | 31 |
| K119T | 62 | T6I | 62 |
| K213T | 25 | E159V/A282V/T319I | 25 |
| K119A/K213A/S11H | 69 | D224G | 69 |
| K119A/K213A/D99V | 56 | A21S/I43F/T165I | 38 |
| K119A/K213A/R167C | 38 | Y82H/R226H/N300S/V304I | 38 |
| K119A/K213A/H62Y | 38 | K250R/N299K | 31 |
| K119A/K213A/M86I | 56 | Q32R | 50 |
| K119A/K213A/S11D | 50 | D63E/D320V | 56 |
| K119A/K213A/T165I | 62 | G254D/S268T | 31 |
| K119A/K213A/M86L | 38 | R46H/L211F | 38 |
| K119A/K213A/K103T | 44 | L157M/L197M | 50 |
| K119A/K213A/S11T | 62 | L157M/T322M | 56 |
| N257D/T322I | 38 | L157M/L197M/T322M | 44 |
| E96K/F116L/K170N/D320G/V328I | 25 | I101F | 50 |
| N315I | 56 | P12IL/Y205N/Q220K | 31 |
| T256R/Y266F | 38 | Y110N/E203D | 31 |
| T38I | 38 | N88T/E198D/Q244H | 50 |
| K271N/T313A | 31 | E96D | 38 |
| I155N/T182N/H326L | 31 | I20M/P121L | 50 |
| N293I/Q308L | 38 | E235K | 56 |
| K119A/K213A/R26A/K73A | 44 | K119A/K213A/R26A/K208A | 44 |
| K119A/K213A/R26A/K111A | 25 | K119A/K213A/R26A/K221A | 38 |
| K119A/K213A/R26A/K200A | 19 | K119A/K213A/R26A/K284A | 38 |
| K119A/K213A | 60 | | |
| pET29a-empty | 0 | | |

Results shown in Table 6 support the finding that at least amino acid positions 119 and 213 in SEQ ID NO:1 are important for determining FAW activity.

Example 3. Testing Txp40 Activity Against Vip3-Resistant FAW

To determine if the toxicity of the Txp40 and/or variant protein is through a different MOA from a Vip3A protein, the Txp40 wild-type and Txp40-K119A variant proteins described above were produced as described in Example 2. The Txp40 proteins were mixed separately in a Txp40 Buffer, and the purity of the dissolved protein preparation was monitored using a Bio-Rad Experion system (BioRad, Hercules, CA).

The purified proteins were tested for efficacy against a strain of FAW that is resistant to a Vip3A insecticidal protein. A diet-overlay assay was performed essentially as described in Example 1. Vip3A protein was dissolved in PBS. The two negative control treatments were PBS and Txp40 Buffer. Cry1Fa protein was used as a positive control for the Vip3A-resistant FAW strain. Multiple concentrations of each protein were tested. Insecticidal activity was assessed as effective mortality on day 7 (larvae that had growth inhibition and were moribund were scored as effectively dead).

Results indicated that the Vip3A-resistant FAW strain is not controlled by Vip3A, demonstrating that the strain is resistant to this protein. In contrast, the Txp40 wild-type protein and the Txp40-K119A variant caused 60% mortality to the Vip3-resistant insects suggesting that the mode of action of Txp40 is different from the mode of action of a Vip3A protein and therefore is useful in a stacking combination with Vip3 to mitigate the development of resistance in a FAW population.

Example 4. Simulated Gastric Fluid Testing on *E. coli* Lysate Preparations

This example describes an assay to determine SGF digestibility of Txp40 and/or Txp40 variants. Each Txp40 protein and/or variant was produced in *E. coli* strain BL21* (DE3). The expression level of the variant in the bacterial strain and the solubility of the variant was determined. Bacterial lysates in a buffer were diluted to 3 mg/mL (total protein concentration) for the digestibility analysis. The digestion reaction was initiated by adding 15 μL lysate to 285 μL simulated gastric fluid [10 Units pepsin/μg protein, or approximately 1579 Units pepsin/mL, in G-Con solution (2 mg/mL sodium chloride, pH 1.2)] at 37° C. At 5 minutes, 100 μL of the lysate-SGF reaction was removed and the reaction terminated by adding it to 100 μL of preheated (95° C.) stop solution comprised of 65 Tricine Loading Buffer (Bio-rad 2× Tricine Load Buffer w/ 10 β-mercaptoethanol) and 35 500 mM sodium bicarbonate, pH 11.0. A zero time (T0) point was produced by adding 5 μL of test lysate to preheated (95° C.) 100 μL Stop Solution and 95 μL of simulated gastric fluid. All samples were heated at 95° C. for 5 minutes, and then stored on ice until SDS-PAGE analysis. Thirty microliters of each reaction were loaded on a 10-20 Tris-tricine peptide gel prior to standard protein gel electrophoresis. The Tris-tricine gel is fixed for 20 minutes with a 40 methanol:10 acetic acid mixture immediately after the electrophoresis. The gel was then stained with GelCode Blue protein stain for 1 hour at room temperature. After 1 hour, the polyacrylamide gel was de-stained with distilled water for at least 12 hours. Results consist of a "Pass" "Fail" assessment. A "Fail" for the T5 test means that intact or partially digested Txp40 protein and/or variant was detectable by GelCode Blue protein stain following gel electrophoresis, indicating that the protein was not fully digestible in the SGF assay. A "Pass" for the T5 Test means intact Txp40 protein and/or variant was not detectable, indicating that the Txp40 protein and/or variant was digestible in the SGF assay. Results of these experiments demonstrated that Txp40 and variant Txp40 proteins are fully digested in the SGF assay.

Example 5. Transformation of Maize with a Txp40-1 Codon-Optimized Gene

A binary vector construct suitable for *Agrobacterium*-mediated transformation of maize is produced. The binary vector comprises a maize optimized nucleic acid encoding txp40-K119A/K213A (SEQ ID NO: 127) and one encoding Txp40-K119A/K213A/S11Y (SEQ ID NO:131), operably linked at the 5' end to a promoter suitable for driving expression in plants and operably linked at the 3'end to a terminator sequence. Maize codon optimization is performed, for example, using the methods described in U.S. Pat. No. 6,320,100 (incorporated herein by reference). The construct is transformed into *Agrobacterium tumefaciens* using standard molecular biology techniques known to those skilled in the art. To prepare the Agrobacteria for transformation, cells are cultured in liquid YPC media at 28° C. and 220 rpm overnight. *Agrobacterium* transformation of immature maize embryos is performed essentially as described in Negrotto et al., 2000, (Plant Cell Reports 19: 798-803). For this example, all media constituents are essentially as described in Negrotto et al., supra. However, various media constituents known in the art may be substituted.

Following transformation, selection, and regeneration, plants are assayed for the presence of the gene encoding the selectable marker and the txp40 maize codon-optimized coding sequence using TaqMan® analysis. Plants are also tested for the presence of the vector backbone. Plants negative for the vector backbone and comprising one copy of the transgene are transferred to the greenhouse and assayed for resistance to FAW damage. Results will show that both proteins express in plants and are active against fall armyworm.

Example 6. Txp40-1 in Combination with a Second Insecticidal Agent

Txp40 and/or a Txp40 variant are purified as bacterial lysates as in Example 1 or purified as proteins. A second insecticidal agent, for example a Cry protein and/or a VIP and/or a dsRNA is prepared. In non-limiting examples, the Cry protein may be a Cry1Ab, a Cry1B, a Cry1C, a Cry1D, a Cry1F, a Cry1J and/or a Cry2A protein. In other non-limiting examples, the Vip3 protein may be a Vip3A and/or a Vip3B protein. dsRNA may target a gene encoding vacuolar ATP synthase, beta-tubulin, 26S proteosome subunit p28 protein, EF1α 48D, troponin I, tetraspanin, gamma-coatomer, beta-coatomer, and/or juvenile hormone epoxide hydrolase (WO Publication Nos. WO2018/026770, WO2018/026773, and WO2018/026774; U.S. Pat. No. 7,812,219; each herein incorporated by reference). Purified Txp40 protein and the second insecticidal agent are tested for insecticidal efficacy against FAW in a diet-overlay assay, performed essentially as described in Example 1 but with the addition of the second insecticidal agent.

It should be understood that the examples and embodiments described herein are for illustrative purposes only and that various modifications or changes in light thereof of the description will be suggested to persons skilled in the art and are to be included within the spirit and purview of this application and the scope of the appended claims.

All publications and patent applications mentioned in this specification are indicative of the level of skill of those skilled in the art that this invention pertains. All publications and patent applications are herein incorporated by reference to the same extent as if each individual publication or patent application was specifically and individually indicated to be incorporated by reference.

What is claimed is:

1. A method of controlling a *Spodoptera frugiperda* insect pest, comprising applying to a plant surface an isolated Txp40 protein or a variant thereof comprising an amino acid sequence selected from the group consisting of:

a) an amino acid sequence having at least 97% identity to SEQ ID NO: 81 and retaining the alanine residue at position 119;

b) an amino acid sequence having at least 97% identity to SEQ ID NO: 89 and retaining the alanine residue at position 213; and c) an amino acid sequence having at least 97% identity to SEQ ID NO: 127 and retaining the alanine residues at positions 119 and 213.

2. The method according to claim 1, wherein said *Spodoptera frugiperda* insect pest is resistant to a Cry protein and/or a Vip3 protein.

3. The method according to claim 2, wherein said Vip3 protein is a Vip3A protein.

4. The method according to claim 2, wherein said Cry protein is a Cry1A, a Cry1B, a Cry1C, a Cry1D, a Cry1F, a Cry1J or a Cry2A protein.

5. The method according to claim 1, wherein said *Spodoptera frugiperda* is contacted with a Cry protein and/or a Vip3 protein in addition to said Txp40 protein or variant thereof.

6. The method according to claim 5, wherein the Cry protein and/or the Vip3 protein is selected from the group consisting of a Cry1A, Cry1B, Cry1C, Cry1D, Cry1F, Cry2A and a Vip3 protein.

7. An insecticidal protein comprising the amino acid sequence of SEQ ID NOs: 74-93, 95-113, 116-119, or 123-136.

8. A transgenic plant infestable by a fall armyworm (*Spodoptera frugiperda*) insect pest and which is protected from said insect pest by being stably transformed with at least one nucleic acid molecule encoding a Txp40 protein or a variant thereof comprising an amino acid sequence selected from the group consisting of:
  - a) an amino acid sequence having at least 97% identity to SEQ ID NO: 81 and retaining the alanine residue at position 119;
  - b) an amino acid sequence having at least 97% identity to SEQ ID NO: 89 and retaining the alanine residue at position 213; and
  - c) an amino acid sequence having at least 97% identity to SEQ ID NO: 127 and retaining the alanine residues at positions 119 and 213.

9. A transgenic plant infestable by a fall armyworm (*Spodoptera frugiperda*) insect pest and which is protected from said insect pest by being stably transformed with at least one nucleic acid molecule encoding an insecticidal protein of claim 7.

10. The transgenic plant according to claim 8, wherein said plant is a corn plant.

11. The transgenic plant according to claim 8, wherein the fall armyworm pest is resistant to a Cry1F protein or a Vip3 protein.

12. A codon-optimized nucleotide sequence encoding a Txp40 protein or variant thereof comprising an amino acid sequence selected from the group consisting of:
  - a) an amino acid sequence having at least 97% identity to SEQ ID NO: 81 and retaining the alanine residue at position 119;
  - b) an amino acid sequence having at least 97% identity to SEQ ID NO: 89 and retaining the alanine residue at position 213; and
  - c) an amino acid sequence having at least 97% identity to SEQ ID NO: 127 and retaining the alanine residues at positions 119 and 213;

and wherein said codons are optimized for expression in a corn plant.

13. The codon-optimized polynucleotide according to claim 12, wherein the nucleotide sequence comprises SEQ ID NOs: 18, 26, or 64.

14. A method of mitigating the development of resistance to a Vip3 protein or a Cry1F protein in a population of fall armyworm (*Spodoptera frugiperda*), the method comprising delivering to the fall armyworm population or an environment thereof a transgenic plant comprising a polynucleotide encoding a Txp40 protein or variant thereof comprising an amino acid sequence selected from the group consisting of:
  - a) an amino acid sequence having at least 97% identity to SEQ ID NO: 81 and retaining the alanine residue at position 119;
  - b) an amino acid sequence having at least 97% identity to SEQ ID NO: 89 and retaining the alanine residue at position 213; and
  - c) an amino acid sequence having at least 97% identity to SEQ ID NO: 127 and retaining the alanine residues at positions 119 and 213;

and a polynucleotide comprising a nucleotide sequence encoding a Vip3A protein or a nucleotide sequence encoding a Cry1F protein; wherein the Txp40 protein or variant thereof and the Vip3 protein or the Cry1F protein are produced in the transgenic plant.

15. A method for producing corn protected against fall armyworm (*Spodoptera frugiperda*), comprising: (a) introducing into a corn plant a polynucleotide encoding a Txp40 protein or variant thereof comprising an amino acid sequence selected from the group consisting of:
  - i) an amino acid sequence having at least 97% identity to SEQ ID NO: 81 and retaining the alanine residue at position 119;
  - ii) an amino acid sequence having at least 97% identity to SEQ ID NO: 89 and retaining the alanine residue at position 213; and
  - iii) an amino acid sequence having at least 97% identity to SEQ ID NO: 127 and retaining the alanine residues at positions 119 and 213;

(b) planting said corn plant or a progeny of said corn plant in a field infestable by a fall armyworm insect pest, wherein said corn plant or said progeny expresses said Txp40 protein.

16. The method according to claim 15, wherein said introducing step is accomplished by a) transforming a corn cell with said polynucleotide and regenerating a corn plant that expresses said Txp40 protein or variant thereof; or b) crossing a first corn plant comprising said polynucleotide with a second corn plant, resulting in a progeny corn plant that expresses said Txp40 protein or variant thereof.

17. The method according to claim 1, wherein the applying is spraying.

* * * * *

SEQUENCE LISTING

```
<160> NUMBER OF SEQ ID NOS: 136

<210> SEQ ID NO 1
<211> LENGTH: 335
<212> TYPE: PRT
<213> ORGANISM: Photorhabdus luminescens

<400> SEQUENCE: 1

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
```

```
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 2
<211> LENGTH: 336
<212> TYPE: PRT
<213> ORGANISM: Artificial Sequence
<220> FEATURE:
<223> OTHER INFORMATION: Variant Txp40-1

<400> SEQUENCE: 2

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Arg Glu Thr
65                  70                  75                  80

Ile Arg Glu Met Glu Asn Thr Ser Asn Leu Ser Ser Ala Leu Leu Gly
                85                  90                  95

Glu Asn Gly Asp Gln Ile Ser Lys Asp Met Ala Asp Gly Phe Tyr Lys
            100                 105                 110

Asn Glu Leu Asp Phe Glu Gly Lys Tyr Pro Gln Asn Ile Trp Asn Ile
        115                 120                 125

Pro Asp Leu Glu Asn Lys Pro Leu Ser Ala Tyr Ser Asp Asp Asp Lys
    130                 135                 140

Leu Leu Ala Leu Tyr Phe Phe Ala Ala Gln Glu Ile Pro Leu Glu Glu
```

-continued

```
145                 150                 155                 160

Asn Gln Gln Ser Asn Thr Ala Arg Phe Phe Lys Leu Ile Asp Phe Leu
                165                 170                 175

Phe Ile Leu Ser Ala Val Thr Ser Leu Gly Arg Arg Ile Phe Ser Lys
            180                 185                 190

Asn Phe Tyr Asn Gly Leu Glu Ser Lys Ser Leu Glu Asn Tyr Ile Glu
        195                 200                 205

Arg Lys Lys Leu Ser Lys Pro Phe Phe Arg Pro Pro Gln Lys Leu Pro
    210                 215                 220

Asp Gly Arg Ile Gly Tyr Leu Ala Ser Pro Thr Glu Pro Pro Lys Trp
225                 230                 235                 240

Arg Val Ser Leu Gln Glu Leu Lys Asn Asn Lys Ser Arg Asn Gly Phe
                245                 250                 255

Thr Asn Met Glu Ser Ala Ala Lys Gln Lys Tyr Ser Ser Phe Ile Lys
            260                 265                 270

Glu Val Gln Lys Gly Asn Asp Pro Leu Thr Ala Ala Lys Ser Ile Gly
        275                 280                 285

Thr Ala Ser Gly Ser Asn Leu Glu Lys Leu Pro Asn Asn Leu Tyr Ser
    290                 295                 300

Val Arg Leu Ser Gln Lys Asp Arg Val Thr Phe Asn Leu Asn Asn Thr
305                 310                 315                 320

Asp Ser Thr Met Thr Ile His Ser Val Gly Thr His Tyr Lys Asn Ile
                325                 330                 335


<210> SEQ ID NO 3
<211> LENGTH: 1008
<212> TYPE: DNA
<213> ORGANISM: Photorhabdus luminescens

<400> SEQUENCE: 3

atggttatac aattaacacc tgataataga agtggatatc cacccgttga aacgcaaata      60

gcaggagata tagtacgttt actaaacttt aagcaaacag atgagggtta tactgcatca     120

catggaattg aatatcgagc taagaaaata atattagcgt acgctttagc tgtaagtggt     180

attcatgatg tatctcatct tcctggtgac tattataaga ataaagagac tgctgaggta     240

atttatcaag aatatatgtc taatctttca tctgcactat taggtgaaaa tggtgatcaa     300

atttctaaag atatggcaga tggtttttac aagaatgagc tggattttga aggtaaatat     360

cctcaaaaca tttggaatat tcctgatctt gaaaataaac cattgagtgc ttattcagat     420

gacgataaat tattagcact atattttttt gctgcacagg aaattccact ggaggaaaat     480

caacaatcaa ataccgcaag attttttaaa ttaattgatt tcttatttat cttatctgct     540

gtaacttcac taggaaggag aatttttttca aaaaactttt acaatgggtt agagtctaaa     600

tcattagaga attatattga gagaaaaaag ctctctaaac ctttctttcg accaccgcag     660

aaattacctg atggcagaat aggttacttg gccagcccaa cagaaccgcc taaatggaga     720

gttagtttgc aagaacttaa aaataacaaa tccaggaatg gatttactaa tatggaaagt     780

gctgcaaaac aaaagtatag ctcatttata aaagaggtgc aaaaggggaa cgatccactg     840

acagcagcaa aaagtattgg tacagcaagc ggcagtaact tggaaaaact gccgaataat     900

ttatatagtg tgaggctaag ccaaaaagac agggtaacct tcaatctaaa taatactgac     960

agtacaatga cgattcatag tgttggaact cattataaaa atatatga                 1008


<210> SEQ ID NO 4
```

-continued

<211> LENGTH: 1008
<212> TYPE: DNA
<213> ORGANISM: Artificial Sequence
<220> FEATURE:
<223> OTHER INFORMATION: E. coli codon-optimized txp40 coding sequence.

<400> SEQUENCE: 4
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tattttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 5
<211> LENGTH: 1008
<212> TYPE: DNA
<213> ORGANISM: Artificial Sequence
<220> FEATURE:
<223> OTHER INFORMATION: Maize codon-optimized txp40 coding sequence.

<400> SEQUENCE: 5
atggtgatcc agctgacccc ggacaacagg tccggctacc cgccggtgga gacccagatc 60
gccggcgaca tcgtgaggct gctgaacttc aagcagaccg acgagggcta caccgcctcc 120
cacggcatcg agtacagggc caagaagatc atcctggcct acgccctggc cgtgtccggc 180
atccacgacg tgtcccacct gccgggcgac tactacaaga acaaggagac cgccgaggtg 240
atctaccagg agtacatgtc caacctgtcc tccgccctgc tgggcgagaa cggcgaccag 300
atctccaagg acatggccga cggcttctac aagaacgagc tggacttcga gggcaagtac 360
ccgcagaaca tctggaacat cccggacctg gagaacaagc cgctgtccgc ctactccgac 420
gacgacaagc tgctggccct gtacttcttc gccgcccagg agatcccgct ggaggagaac 480
cagcagtcca acaccgccag gttcttcaag ctgatcgact tcctgttcat cctgtccgcc 540
gtgacctccc tgggcaggag gatcttctcc aagaacttct acaacggcct ggagtccaag 600
tccctggaga actacatcga gaggaagaag ctgtccaagc cgttcttcag gccgccgcag 660
aagctgccgg acggcaggat cggctacctg gcctccccga ccgagccgcc gaagtggagg 720
gtgtccctgc aggagctgaa gaacaacaag tccaggaacg gcttcaccaa catggagtcc 780
gccgccaagc agaagtactc ctccttcatc aaggaggtgc agaagggcaa cgacccgctg 840

```
accgccgcca agtccatcgg caccgcctcc ggctccaacc tggagaagct gccgaacaac    900

ctgtactccg tgaggctgtc ccagaaggac agggtgacct tcaacctgaa caacaccgac    960

tccaccatga ccatccactc cgtgggcacc cactacaaga acatctga                1008


<210> SEQ ID NO 6
<211> LENGTH: 335
<212> TYPE: PRT
<213> ORGANISM: Photorhabdus luminescens

<400> SEQUENCE: 6

Met Val Ile Gln Leu Thr Pro Asp Asp Arg Ser Gly Tyr Gln Pro Val
1               5                   10                  15

Glu Lys Gln Ile Ala Gly Glu Ile Ile Arg Val Leu Asn Phe Lys Gln
            20                  25                  30

Thr Asp Glu Gly Tyr Thr Ala Ser His Gly Val Glu Tyr Arg Ala Lys
        35                  40                  45

Lys Ile Ile Leu Ala Tyr Ala Leu Ala Val Ser Gly Ile His Asp Val
    50                  55                  60

Ser Gln Leu Pro Gly Asp Tyr Tyr Lys Asn Lys Glu Thr Ala Glu Gly
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Glu Tyr Pro Gln Asn Ile Trp Asn Ile Pro
        115                 120                 125

Asp Leu Glu Asn Lys Pro Leu Ser Asp Tyr Leu Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Ala Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Gly Pro Thr Glu Pro Pro Lys Trp Arg
225                 230                 235                 240

Val Ser Phe Gln Glu Leu Lys Lys Asn Arg Ala Arg Asn Gly Phe Ala
                245                 250                 255

Asn Met Asp Gly Ala Ala Lys Gln Lys Tyr Ser Ser Phe Val Lys Glu
            260                 265                 270

Val Gln Lys Gly Asn Asp Pro Leu Thr Ala Ala Lys Ser Val Gly Thr
        275                 280                 285

Ala Ser Gly Ser Asn Leu Glu Lys Leu Pro Asn Asn Leu Phe Ser Val
    290                 295                 300

Arg Leu Ser Gln Lys Asp Arg Val Thr Phe Thr Gln Asn Asn Thr Glu
305                 310                 315                 320

Asn Thr Ile Thr Ile His Ser Val Gly Thr His Tyr Lys Asn Ile
                325                 330                 335
```

<210> SEQ ID NO 7
<211> LENGTH: 335
<212> TYPE: PRT
<213> ORGANISM: Photorhabdus luminescens

<400> SEQUENCE: 7

| Met | Val | Ile | Gln | Leu | Thr | Pro | Asp | Asp | Arg | Ser | Gly | Tyr | Pro | Pro | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Glu | Lys | Gln | Ile | Ala | Gly | Asp | Ile | Val | Arg | Ile | Leu | Asn | Phe | Lys | Gln |
|     |     |     | 20  |     |     |     |     | 25  |     |     |     |     | 30  |     |     |

| Thr | Asp | Glu | Gly | His | Thr | Ala | Ser | Tyr | Gly | Ile | Glu | Tyr | Arg | Ala | Lys |
|     |     | 35  |     |     |     |     | 40  |     |     |     |     | 45  |     |     |     |

| Lys | Ile | Ile | Leu | Ala | Tyr | Ala | Leu | Ala | Val | Ser | Gly | Ile | His | Asn | Val |
|     | 50  |     |     |     |     | 55  |     |     |     |     | 60  |     |     |     |     |

| Ser | Gln | Leu | Pro | Asp | Asp | Tyr | Tyr | Lys | Asn | Lys | Glu | Thr | Ala | Glu | Arg |
| 65  |     |     |     |     | 70  |     |     |     |     | 75  |     |     |     |     | 80  |

| Ile | Tyr | Gln | Glu | Tyr | Met | Ser | Asn | Leu | Ser | Ser | Ala | Leu | Leu | Gly | Glu |
|     |     |     |     | 85  |     |     |     |     | 90  |     |     |     |     | 95  |     |

| Asn | Gly | Asp | Gln | Ile | Ser | Lys | Asp | Met | Ala | Asn | Gly | Phe | Tyr | Lys | Asn |
|     |     |     | 100 |     |     |     |     | 105 |     |     |     |     | 110 |     |     |

| Glu | Leu | Asp | Phe | Glu | Gly | Gln | Tyr | Pro | Gln | Asn | Ile | Trp | Asn | Val | Pro |
|     |     |     | 115 |     |     |     |     | 120 |     |     |     |     | 125 |     |     |

| Glu | Leu | Glu | Asn | Lys | Pro | Leu | Ser | Ala | Tyr | Ser | Asp | Asp | Asp | Lys | Leu |
|     | 130 |     |     |     |     | 135 |     |     |     |     | 140 |     |     |     |     |

| Leu | Ala | Leu | Tyr | Phe | Phe | Ser | Val | Gln | Glu | Ile | Pro | Leu | Glu | Glu | Asn |
| 145 |     |     |     |     | 150 |     |     |     |     | 155 |     |     |     |     | 160 |

| Gln | Gln | Ser | Asn | Ala | Ala | Arg | Phe | Phe | Lys | Leu | Ile | Asp | Phe | Leu | Phe |
|     |     |     |     | 165 |     |     |     |     | 170 |     |     |     |     | 175 |     |

| Ile | Leu | Ser | Ala | Val | Thr | Ser | Leu | Gly | Arg | Arg | Ile | Phe | Ser | Lys | Asn |
|     |     |     | 180 |     |     |     |     | 185 |     |     |     |     | 190 |     |     |

| Phe | Tyr | Asn | Gly | Leu | Glu | Ser | Lys | Ser | Leu | Glu | Asn | Tyr | Ile | Glu | Arg |
|     |     | 195 |     |     |     |     | 200 |     |     |     |     | 205 |     |     |     |

| Lys | Lys | Leu | Ser | Lys | Pro | Phe | Phe | Arg | Pro | Pro | Gln | Lys | Leu | Pro | Asp |
|     | 210 |     |     |     |     | 215 |     |     |     |     | 220 |     |     |     |     |

| Gly | Arg | Ile | Gly | Tyr | Leu | Ala | Ser | Pro | Thr | Glu | Pro | Pro | Lys | Trp | Arg |
| 225 |     |     |     |     | 230 |     |     |     |     | 235 |     |     |     |     | 240 |

| Val | Ser | Phe | Gln | Glu | Leu | Lys | Lys | Asn | Lys | Ser | Arg | Asn | Gly | Phe | Tyr |
|     |     |     |     | 245 |     |     |     |     | 250 |     |     |     |     | 255 |     |

| Asn | Met | Asp | Arg | Ala | Ala | Gln | Gln | Lys | Tyr | Ser | Ser | Phe | Ile | Lys | Glu |
|     |     |     | 260 |     |     |     |     | 265 |     |     |     |     | 270 |     |     |

| Val | Gln | Lys | Gly | Asn | Asp | Pro | Leu | Thr | Ala | Ala | Lys | Ser | Ile | Gly | Thr |
|     |     | 275 |     |     |     |     | 280 |     |     |     |     | 285 |     |     |     |

| Ala | Ser | Gly | Ser | Asn | Leu | Glu | Lys | Leu | Pro | Asn | Asn | Leu | Tyr | Ser | Val |
|     | 290 |     |     |     |     | 295 |     |     |     |     | 300 |     |     |     |     |

| Arg | Leu | Ser | Lys | Glu | Asp | Arg | Val | Thr | Phe | Thr | Gln | Asn | Asn | Thr | Asp |
| 305 |     |     |     |     | 310 |     |     |     |     | 315 |     |     |     |     | 320 |

| Asn | Thr | Met | Thr | Val | His | Ser | Val | Gly | Thr | His | Tyr | Lys | Asn | Ile |
|     |     |     |     | 325 |     |     |     |     | 330 |     |     |     |     | 335 |

<210> SEQ ID NO 8
<211> LENGTH: 335
<212> TYPE: PRT
<213> ORGANISM: Photorhabdus luminescens

<400> SEQUENCE: 8

Met Val Ile Gln Leu Thr Pro Asp Asp Arg Ser Gly Tyr Gln Pro Val

-continued

```
1               5                   10                  15

Glu Lys Gln Ile Ala Gly Glu Ile Ile Arg Val Leu Asn Phe Lys Gln
            20                  25                  30

Thr Asp Glu Gly Tyr Thr Ala Ser His Gly Val Glu Tyr Arg Ala Lys
        35                  40                  45

Lys Ile Ile Leu Ala Tyr Ala Leu Ala Val Ser Gly Ile His Asp Val
    50                  55                  60

Ser Gln Leu Pro Gly Asp Cys Tyr Lys Asn Lys Glu Thr Ala Glu Gly
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Glu Tyr Pro Gln Asn Ile Trp Asn Ile Pro
        115                 120                 125

Asp Leu Glu Asn Lys Pro Leu Ser Asp Tyr Leu Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Ala Ala Arg Phe Phe Lys Leu Ile Asp Phe Leu Phe
                165                 170                 175

Ile Leu Ser Ala Val Thr Ser Leu Gly Arg Arg Ile Ser Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Gly Pro Thr Glu Pro Pro Lys Trp Arg
225                 230                 235                 240

Val Ser Phe Gln Glu Leu Lys Lys Asp Arg Ala Arg Asn Gly Phe Ala
                245                 250                 255

Asn Met Asp Gly Ala Ala Lys Gln Lys Tyr Ser Ser Phe Val Lys Glu
            260                 265                 270

Val Gln Lys Gly Asn Asp Pro Leu Thr Ala Ala Arg Ser Val Gly Thr
        275                 280                 285

Ala Ser Gly Ser Asn Leu Glu Lys Leu Pro Asn Asn Leu Phe Ser Val
    290                 295                 300

Arg Leu Ser Gln Lys Asp Arg Val Thr Phe Thr Gln Asn Asn Thr Glu
305                 310                 315                 320

Asn Thr Ile Thr Ile His Ser Val Gly Thr His Tyr Lys Asn Ile
                325                 330                 335


<210> SEQ ID NO 9
<211> LENGTH: 335
<212> TYPE: PRT
<213> ORGANISM: Photorhabdus luminescens

<400> SEQUENCE: 9

Met Val Ile Gln Leu Thr Pro Asp Asp Arg Ser Gly Tyr Pro Pro Val
1               5                   10                  15

Glu Lys Gln Ile Ala Gly Asp Ile Val Arg Ile Leu Asn Phe Lys Gln
            20                  25                  30

Thr Asp Glu Gly His Thr Ala Ser Tyr Gly Ile Glu Tyr Arg Ala Lys
        35                  40                  45
```

```
Lys Ile Ile Leu Ala Tyr Ala Leu Ala Val Ser Gly Ile His Asn Val
    50                  55                  60

Ser Gln Leu Pro Asp Asp Tyr Tyr Lys Asn Lys Glu Thr Ala Glu Arg
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asn Gly Phe Tyr Lys Asn
            100                 105                 110

Glu Leu Asp Phe Glu Gly Gln Tyr Pro Gln Asn Ile Trp Asn Val Pro
        115                 120                 125

Glu Leu Glu Asn Lys Pro Leu Ser Ala Tyr Ser Asp Asp Asp Lys Leu
    130                 135                 140

Leu Ala Leu Tyr Phe Phe Ser Val Gln Glu Ile Pro Leu Glu Glu Asn
145                 150                 155                 160

Gln Gln Ser Asn Ala Ala Arg Phe Phe Lys Leu Ile Asp Phe Leu Phe
                165                 170                 175

Thr Leu Ser Ala Val Thr Ser Leu Gly Arg Arg Ile Phe Ser Lys Asn
            180                 185                 190

Phe Tyr Asn Gly Leu Glu Ala Lys Ser Leu Glu Asn Tyr Ile Glu Arg
        195                 200                 205

Lys Lys Leu Ser Lys Pro Phe Phe Arg Pro Pro Gln Arg Leu Pro Asp
    210                 215                 220

Gly Arg Ile Gly Tyr Leu Ala Gly Pro Thr Glu Ala Pro Lys Trp Arg
225                 230                 235                 240

Val Ser Phe Lys Glu Leu Lys Asn Asn Lys Ser Arg Asn Gly Phe Ser
                245                 250                 255

Asn Met Glu Arg Ala Ala Lys Gln Lys Tyr Ser Ser Phe Ile Lys Glu
            260                 265                 270

Val Gln Lys Gly Asn Ala Pro Gln Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Thr Gln Asn Asp Thr Asp
305                 310                 315                 320

Asn Thr Met Thr Val His Ser Val Gly Thr His Tyr Lys Asn Ile
                325                 330                 335


<210> SEQ ID NO 10
<211> LENGTH: 362
<212> TYPE: PRT
<213> ORGANISM: Xenorhabdus nematophila

<400> SEQUENCE: 10

Met Val Ile Lys Pro Val Thr Thr Pro Ser Val Ile Gln Leu Thr Pro
1               5                   10                  15

Asp Asp Arg Glu Asp Tyr Gln Pro Val Glu Lys Gln Ile Ala Gly Asp
            20                  25                  30

Ile Ile Arg Val Leu Asn Phe Lys Gln Thr Asn Glu Ser His Thr Ile
        35                  40                  45

Asn Tyr Gly Ile Ala Tyr Arg Ala Lys Lys Val Ile Ile Ala Tyr Ala
    50                  55                  60

Leu Ala Val Ser Gly Ile His Asn Val Ser Gln Leu Pro Glu Asp Tyr
65                  70                  75                  80

Tyr Lys Asn Lys Asp Asn Thr Gly Arg Ile Tyr Gln Glu Tyr Met Ser
                85                  90                  95
```

-continued

```
Asn Leu Lys Ser Ala Leu Leu Gly Glu Asn Gly Asp Gln Ile Ser Lys
            100                 105                 110

Asp Met Ala Asn Asp Phe Thr Gln Asn Glu Leu Glu Phe Gly Gly Gln
        115                 120                 125

Arg Tyr Gln Asn Thr Trp Asp Ile Pro Asp Leu Glu Asn Lys Leu Leu
    130                 135                 140

Glu Asp Tyr Ser Asp Asp Asp Lys Leu Leu Ala Leu Tyr Phe Phe Asp
145                 150                 155                 160

Phe Gln Glu Leu Pro Met Glu Leu Asn Gln Gln Ser Asn Ala Ala Asn
                165                 170                 175

Phe Phe Lys Val Ile Asp Phe Leu Phe Lys Leu Ser Ala Val Thr Ser
            180                 185                 190

Leu Gly Lys Arg Ile Phe Ser Lys Asn Phe Tyr Asn Gly Leu Glu Ala
        195                 200                 205

Lys Ser Leu Glu Asn Tyr Ile Glu Arg Lys Lys Leu Ser Lys Pro Phe
    210                 215                 220

Phe Arg Pro Pro Gln Lys Leu Pro Asp Gly Arg Thr Gly Tyr Leu Ala
225                 230                 235                 240

Gly Pro Glu Glu Ala Pro Lys Leu Pro Thr Thr Ser Ser Thr Ala Thr
                245                 250                 255

Thr Ser Thr Ala Ala Ser Ser Asn Trp Arg Val Ser Leu Gln Lys Leu
            260                 265                 270

Arg Asp Asn Pro Ser Arg Asn Gly Phe Met Asn Met Asp Asp Ala Ala
        275                 280                 285

Lys Arg Lys Tyr Ser Ser Phe Ile Lys Glu Val Gln Lys Gly Asn Asp
    290                 295                 300

Pro Gln Ala Ala Ala Lys Ser Ile Gly Thr Lys Ser Gly Ser Asn Phe
305                 310                 315                 320

Glu Lys Leu Gln Gly Arg Asp Leu Tyr Ser Ile Arg Leu Ser Gln Glu
                325                 330                 335

His Arg Val Thr Phe Ser Ile Asn Asn Thr Asp Gln Ile Met Glu Ile
            340                 345                 350

Gln Ser Val Gly Thr His Tyr Gln Asn Ile
        355                 360
```

<210> SEQ ID NO 11
<211> LENGTH: 1008
<212> TYPE: DNA
<213> ORGANISM: Artificial Sequence
<220> FEATURE:
<223> OTHER INFORMATION: E. coli codon optimized coding sequence for
      Txp40_1 K31A mutant

<400> SEQUENCE: 11

```
atggtgattc agttgactcc ggataatcgt tctgggtatc cacccgttga gacgcagatc     60

gctggagaca ttgtgcgctt gttgaatttc gctcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480
```

-continued

```
caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                 1008
```

<210> SEQ ID NO 12
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K48A mutant

<400> SEQUENCE: 12

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc ggctaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                 1008
```

<210> SEQ ID NO 13
<211> LENGTH: 1008
<212> TYPE: DNA
<213> ORGANISM: Artificial Sequence
<220> FEATURE:
<223> OTHER INFORMATION: E. coli codon optimized coding sequence for
      Txp40_1 K49A mutant

<400> SEQUENCE: 13

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaagctatc attttagctt atgcgttagc ggtttcagga    180
```

atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 14
<211> LENGTH: 1008
<212> TYPE: DNA
<213> ORGANISM: Artificial Sequence
<220> FEATURE:
<223> OTHER INFORMATION: E. coli codon optimized coding sequence for Txp40_1 K73A mutant

<400> SEQUENCE: 14
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacgcta acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 15
<211> LENGTH: 1008
<212> TYPE: DNA
<213> ORGANISM: Artificial sequence

```
<220> FEATURE:
<223> OTHER INFORMATION: E. coli codon optimized coding sequence for
      Txp40_1 K75A mutant

<400> SEQUENCE: 15

atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acgctgaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008


<210> SEQ ID NO 16
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K103A mutant

<400> SEQUENCE: 16

atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctgctg acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840
```

-continued

```
accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008


<210> SEQ ID NO 17
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K111A mutant

<400> SEQUENCE: 17

atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac gctaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008


<210> SEQ ID NO 18
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K119A mutant

<400> SEQUENCE: 18

atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggagcttac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540
```

```
gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 19
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K133A mutant

<400> SEQUENCE: 19

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacgctc ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 20
<211> LENGTH: 1008
<212> TYPE: DNA
<213> ORGANISM: Artificial Sequence
<220> FEATURE:
<223> OTHER INFORMATION: E. coli codon optimized coding sequence for
Txp40_1 K143A mutant

<400> SEQUENCE: 20

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180
```

-continued

```
atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgatgctc ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 21
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K170A mutant

<400> SEQUENCE: 21

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttgct ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 22
<211> LENGTH: 1008
<212> TYPE: DNA
<213> ORGANISM: Artificial sequence
<220> FEATURE:

<223> OTHER INFORMATION: E. coli codon optimized coding sequence for
      Txp40_1 K191A mutant

<400> SEQUENCE: 22
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt gctaattttt acaacgggct tgaatccaaa 600
tcgttagaga actacatcga acgcaagaaa ctttcgaaac ctttcttccg cccaccccag 660
aaacttccgg acggtcgtat cggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 23
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K200A mutant

<400> SEQUENCE: 23
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccgct 600
tcgttagaga actacatcga acgcaagaaa ctttcgaaac ctttcttccg cccaccccag 660
aaacttccgg acggtcgtat cggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 24
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K209A mutant

<400> SEQUENCE: 24
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccaaa 600
tcgttagaga actacatcga acgcgctaaa ctttcgaaac ctttcttccg cccaccccag 660
aaacttccgg acggtcgtat cggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 25
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K210A mutant

<400> SEQUENCE: 25
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540

```
gtgacttccc ttgggcgtcg tatttttagt aaaaattttt acaacgggct tgaatccaaa    600

tcgttagaga actacatcga acgcaaggct ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 26
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K213A mutant

<400> SEQUENCE: 26

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 27
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K221A mutant

<400> SEQUENCE: 27

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240
```

```
atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

gctcttccgg acggtcgtat cggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 28
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K238A mutant

<400> SEQUENCE: 28

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cggtacctg gcttcgccca ccgaaccacc cgcttggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 29
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K247A mutant

<400> SEQUENCE: 29
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg cttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctggc taataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 30
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K250A mutant

<400> SEQUENCE: 30
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg cttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataatgct tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900

-continued ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 31
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K263A mutant

<400> SEQUENCE: 31
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cggtacctg gcttcgccca ccgaaccacc caagtggcgc 720
gttagtttac aggagctgaa aaataataaa tctcgcaacg gattcacgaa catggagtcc 780
gctgcggctc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 32
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K265A mutant

<400> SEQUENCE: 32
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg cttttttaag ttaattgact ttcttttcat tctttcggcc 540
gtgacttccc ttgggcgtcg tatttttagt aaaaattttt acaacgggct tgaatccaaa 600

```
tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aagcttactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa              1008
```

<210> SEQ ID NO 33
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K271A mutant

<400> SEQUENCE: 33

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt gctgaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa              1008
```

<210> SEQ ID NO 34
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K275A mutant

<400> SEQUENCE: 34

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240
```

-continued

```
atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aagctgggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 35
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K284A mutant

<400> SEQUENCE: 35

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcgg cttcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 36
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K296A mutant

<400> SEQUENCE: 36
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaagctct gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 37
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K309A mutant

<400> SEQUENCE: 37
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaagctgac cgcgtgacct ttaatctgaa taatactgac 960
agtaccatga cgatccattc tgtaggcact cactacaaaa atatctaa 1008

<210> SEQ ID NO 38
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K333A mutant

<400> SEQUENCE: 38
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacgcta atatctaa 1008

<210> SEQ ID NO 39
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R10A mutant

<400> SEQUENCE: 39
atggtgattc agttgactcc ggataatgct tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 40
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R26A mutant

<400> SEQUENCE: 40
atggtgattc agttgactcc ggataatcgt tctgggtatc cacccgttga gacgcagatc 60
gctggagaca ttgtggcttt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaaatttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 41
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R46A mutant

<400> SEQUENCE: 41
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatgctgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300

```
atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 42
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R167A mutant

<400> SEQUENCE: 42

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagccgc tttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 43
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R186A mutant

<400> SEQUENCE: 43
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttggggctcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 44
<211> LENGTH: 1008
<212> TYPE: DNA
<213> ORGANISM: Artificial Sequence
<220> FEATURE:
<223> OTHER INFORMATION: E. coli codon optimized coding sequence for
Txp40_1 R187A mutant

<400> SEQUENCE: 44
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtgc tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960

```
agtaccatga cgatccattc tgtaggcact cactacaaaa atatctaa               1008


<210> SEQ ID NO 45
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 R208A mutant

<400> SEQUENCE: 45

atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc     540

gtgacttccc ttgggcgtcg tatttttagt aaaaattttt acaacgggct tgaatccaaa    600

tcgttagaga actacatcga agctaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008


<210> SEQ ID NO 46
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 R217A mutant

<400> SEQUENCE: 46

atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc     540

gtgacttccc ttgggcgtcg tatttttagt aaaaattttt acaacgggct tgaatccaaa    600

tcgttagaga actacatcga acgcaagaaa ctttcgaaac ctttcttcgc tccaccccag    660
```

aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 47
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R226A mutant

<400> SEQUENCE: 47
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtgctat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 48
<211> LENGTH: 1008
<212> TYPE: DNA
<213> ORGANISM: Artificial Sequence
<220> FEATURE:
<223> OTHER INFORMATION: E. coli codon optimized coding sequence for Txp40_1 R240A mutant

<400> SEQUENCE: 48
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300

```
atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc     540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtgggct    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 49
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 R252A mutant

<400> SEQUENCE: 49

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc     540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctgctaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 50
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 R305A mutant

<400> SEQUENCE: 50
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tagctttgtc ccaaaaggac cgcgtgacct ttaatctgaa taatactgac 960
agtaccatga cgatccattc tgtaggcact cactacaaaa atatctaa 1008

<210> SEQ ID NO 51
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R311A mutant

<400> SEQUENCE: 51
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcgaaac ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac gctgtgacct ttaatctgaa taatactgac 960
agtaccatga cgatccattc tgtaggcact cactacaaaa atatctaa 1008

<210> SEQ ID NO 52
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 double mutant K31A/K49A

<400> SEQUENCE: 52

```
atggtgattc agttgactcc ggataatcgt tctgggtatc cacccgttga gacgcagatc     60

gctggagaca ttgtgcgctt gttgaatttc gctcaaactg acgagggcta cactgcaagt    120

catggaattg aatatcgtgc gaaagctatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 53
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 double mutant K31A/K333A

<400> SEQUENCE: 53

```
atggtgattc agttgactcc ggataatcgt tctgggtatc cacccgttga gacgcagatc     60

gctggagaca ttgtgcgctt gttgaatttc gctcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660
```

```
aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacgcta atatctaa               1008
```

<210> SEQ ID NO 54
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K31A/R208A double mutant

<400> SEQUENCE: 54

```
atggtgattc agttgactcc ggataatcgt tctgggtatc cacccgttga gacgcagatc     60

gctggagaca ttgtgcgctt gttgaatttc gctcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga agctaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 55
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 R208A/K333A double mutant

<400> SEQUENCE: 55

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360
```

```
cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga agctaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacgcta atatctaa                1008
```

<210> SEQ ID NO 56
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K49A/R208A double mutant

<400> SEQUENCE: 56

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaagctatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga agctaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 57
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K49A/K333A double mutant

<400> SEQUENCE: 57

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaagctatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacgcta atatctaa                1008
```

<210> SEQ ID NO 58
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K31A/K49A/K333A mutant

<400> SEQUENCE: 58

```
atggtgattc agttgactcc ggataatcgt tctgggtatc cacccgttga gacgcagatc     60

gctggagaca ttgtgcgctt gttgaatttc gctcaaactg acgagggcta cactgcaagt    120

catggaattg aatatcgtgc gaaagctatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcgaaac ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacgcta atatctaa                1008
```

<210> SEQ ID NO 59
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K31A/K49A/R208A/K333A mutant

<400> SEQUENCE: 59

```
atggtgattc agttgactcc ggataatcgt tctgggtatc cacccgttga gacgcagatc     60
gctggagaca ttgtgcgctt gttgaatttc gctcaaactg acgagggcta cactgcaagt    120
catggaattg aatatcgtgc gaaagctatc attttagctt atgcgttagc ggtttcagga    180
atccatgatg tatcccatct gcctggcgac tattacaaga acaaggaaac ggcagaggtt    240
atttatcagg agtatatgtc taatttgtcg tccgcactgc tgggagagaa cggcgatcag    300
atctctaaag acatggccga cggtttctac aagaacgagc tggatttcga aggaaagtac    360
cctcagaata tctggaatat cccagacttg gaaaacaaac ctttgtcagc gtatagcgac    420
gacgataaac ttttggccct ttatttcttc gcagcacagg agattccgct ggaagagaat    480
caacaaagta atacagcccg ctttttaag ttaattgact ttcttttcat tctttcggcc    540
gtgacttccc ttgggcgtcg tatttttagt aaaaattttt acaacgggct tgaatccaaa    600
tcgttagaga actacatcga agctaagaaa ctttcgaaac ctttcttccg cccaccccag    660
aaacttccgg acggtcgtat cgggtacctg gcttcgccca ccgaaccacc caagtggcgc    720
gttagtttac aggagctgaa aaataataaa tctcgcaacg gattcacgaa catggagtcc    780
gctgcgaagc aaaaatactc atcgtttatt aaagaagttc aaaaggggaa cgatccgtta    840
accgcagcga agtcgatcgg gacggcctct ggttctaact tagaaaaact gcctaataac    900
ttgtattctg tacgcttgtc ccaaaaggac cgcgtgacct ttaatctgaa taatactgac    960
agtaccatga cgatccattc tgtaggcact cactacgcta atatctaa                1008
```

<210> SEQ ID NO 60
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K73A/K213A double mutant

<400> SEQUENCE: 60

```
atggtgattc agttgactcc ggataatcgt tctgggtatc cacccgttga gacgcagatc     60
gctggagaca ttgtgcgctt gttgaatttc aagcaaactg acgagggcta cactgcaagt    120
catggaattg aatatcgtgc gaaaaagatc attttagctt atgcgttagc ggtttcagga    180
atccatgatg tatcccatct gcctggcgac tattacgcta acaaggaaac ggcagaggtt    240
atttatcagg agtatatgtc taatttgtcg tccgcactgc tgggagagaa cggcgatcag    300
atctctaaag acatggccga cggtttctac aagaacgagc tggatttcga aggaaagtac    360
cctcagaata tctggaatat cccagacttg gaaaacaaac ctttgtcagc gtatagcgac    420
gacgataaac ttttggccct ttatttcttc gcagcacagg agattccgct ggaagagaat    480
caacaaagta atacagcccg ctttttaag ttaattgact ttcttttcat tctttcggcc    540
gtgacttccc ttgggcgtcg tatttttagt aaaaattttt acaacgggct tgaatccaaa    600
tcgttagaga actacatcga acgcaagaaa ctttcggctc ctttcttccg cccaccccag    660
aaacttccgg acggtcgtat cgggtacctg gcttcgccca ccgaaccacc caagtggcgc    720
```

gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 61
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K103A/K213A double mutant

<400> SEQUENCE: 61
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctgctg acatggccga cggtttctac aagaacgagc tggatttcga aggaaagtac 360
cctcagaata tctggaatat cccagacttg gaaaacaaac ctttgtcagc gtatagcgac 420
gacgataaac ttttggccct ttatttcttc gcagcacagg agattccgct ggaagagaat 480
caacaaagta atacagcccg ctttttttaag ttaattgact ttcttttcat tctttcggcc 540
gtgacttccc ttgggcgtcg tatttttagt aaaaattttt acaacgggct tgaatccaaa 600
tcgttagaga actacatcga acgcaagaaa ctttcggctc ctttcttccg cccaccccag 660
aaacttccgg acggtcgtat cgggtacctg gcttcgccca ccgaaccacc caagtggcgc 720
gttagtttac aggagctgaa aaataataaa tctcgcaacg gattcacgaa catggagtcc 780
gctgcgaagc aaaaatactc atcgtttatt aaagaagttc aaaaggggaa cgatccgtta 840
accgcagcga agtcgatcgg gacggcctct ggttctaact tagaaaaact gcctaataac 900
ttgtattctg tacgcttgtc ccaaaaggac cgcgtgacct ttaatctgaa taatactgac 960
agtaccatga cgatccattc tgtaggcact cactacaaaa atatctaa 1008

<210> SEQ ID NO 62
<211> LENGTH: 1008
<212> TYPE: DNA
<213> ORGANISM: Artificial Sequence
<220> FEATURE:
<223> OTHER INFORMATION: E. coli codon optimized coding sequence for
Txp40_1 K213A/K284A double mutant

<400> SEQUENCE: 62
atggtgattc agttgactcc ggataatcgt tctgggtatc cacccgttga gacgcagatc 60
gctggagaca ttgtgcgctt gttgaatttc aagcaaactg acgagggcta cactgcaagt 120
catggaattg aatatcgtgc gaaaaagatc attttagctt atgcgttagc ggtttcagga 180
atccatgatg tatcccatct gcctggcgac tattacaaga acaaggaaac ggcagaggtt 240
atttatcagg agtatatgtc taatttgtcg tccgcactgc tgggagagaa cggcgatcag 300
atctctaaag acatggccga cggtttctac aagaacgagc tggatttcga aggaaagtac 360

```
cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcgg cttcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

```
<210> SEQ ID NO 63
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K31A/K49A/K213A mutant

<400> SEQUENCE: 63

atggtgattc agttgactcc ggataatcgt tctgggtatc cacccgttga gacgcagatc     60

gctggagaca ttgtgcgctt gttgaatttc gctcaaactg acgagggcta cactgcaagt    120

catggaattg aatatcgtgc gaaagctatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg ctttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

```
<210> SEQ ID NO 64
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K119A/K213A double mutant

<400> SEQUENCE: 64

atggtgattc agttgactcc ggataatcgt tctgggtatc cacccgttga gacgcagatc     60
```

```
gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggagcttac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 65
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K213A/R167A double mutant

<400> SEQUENCE: 65

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggaaagtac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagccgc ttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa                1008
```

<210> SEQ ID NO 66
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K119A/R167A double mutant

<400> SEQUENCE: 66

```
atggtgattc agttgactcc ggataatcgt tctgggtatc cacccgttga gacgcagatc     60
gctggagaca ttgtgcgctt gttgaatttc aagcaaactg acgagggcta cactgcaagt    120
catggaattg aatatcgtgc gaaaaagatc attttagctt atgcgttagc ggtttcagga    180
atccatgatg tatcccatct gcctggcgac tattacaaga acaaggaaac ggcagaggtt    240
atttatcagg agtatatgtc taatttgtcg tccgcactgc tgggagagaa cggcgatcag    300
atctctaaag acatggccga cggtttctac aagaacgagc tggatttcga aggagcttac    360
cctcagaata tctggaatat cccagacttg gaaaacaaac ctttgtcagc gtatagcgac    420
gacgataaac ttttggccct ttatttcttc gcagcacagg agattccgct ggaagagaat    480
caacaaagta atacagccgc tttttttaag ttaattgact ttcttttcat tctttcggcc    540
gtgacttccc ttgggcgtcg tatttttagt aaaaattttt acaacgggct tgaatccaaa    600
tcgttagaga actacatcga acgcaagaaa ctttcgaaac ctttcttccg cccaccccag    660
aaacttccgg acggtcgtat cgggtacctg gcttcgccca ccgaaccacc caagtggcgc    720
gttagtttac aggagctgaa aaataataaa tctcgcaacg gattcacgaa catggagtcc    780
gctgcgaagc aaaaatactc atcgtttatt aaagaagttc aaaaggggaa cgatccgtta    840
accgcagcga agtcgatcgg gacggcctct ggttctaact tagaaaaact gcctaataac    900
ttgtattctg tacgcttgtc ccaaaaggac cgcgtgacct ttaatctgaa taatactgac    960
agtaccatga cgatccattc tgtaggcact cactacaaaa atatctaa                1008
```

<210> SEQ ID NO 67
<211> LENGTH: 1008
<212> TYPE: DNA
<213> ORGANISM: Artificial sequence
<220> FEATURE:
<223> OTHER INFORMATION: E. coli codon optimized coding sequence for Txp40_1 S11Y/M86I/K119A/K213T mutant

<400> SEQUENCE: 67

```
atggtgattc agttgactcc ggataatcgt tatgggtatc cacccgttga gacgcagatc     60
gctggtgaca ttgtgcgctt attgaatttc aagcaaactg acgagggcta cactgcaagt    120
catggaattg aatatcgtgc gaaaaagatc attttagctt atgcgttagc ggtttcagga    180
atccatgatg tatcccatct gcctggcgac tattacaaga acaaggaaac ggcagaggtt    240
atttatcagg agtatatatc taatttgtcg tccgcactgc tgggagagaa cggcgatcag    300
atctctaaag acatggccga cggtttctac aagaacgagc tggatttcga aggagcttac    360
cctcagaata tctggaatat cccagacttg gaaaacaaac ctttgtcagc gtatagcgac    420
gacgataaac ttttggccct ttatttcttc gcagcacagg agattccgct ggaagagaat    480
caacaaagta atacagcccg ctttttttaag ttaattgact ttcttttcat tctttcggcc    540
gtgacttccc ttgggcgtcg tatttttagt aaaaattttt acaacgggct tgaatccaaa    600
tcgttagaga actacatcga acgcaagaaa ctttcgactc ctttcttccg cccaccccag    660
aaacttccgg acggtcgtat cgggtacctg gcttcgccca ccgaaccacc caagtggcgc    720
```

-continued

```
gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacat ttaatctgaa taatactgac    960

agtaccatga cgatccattc tgtaggcact cactacaaaa atatctaa               1008
```

<210> SEQ ID NO 68
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 S11Y/K119A/K213A mutant

<400> SEQUENCE: 68

```
atggtgattc agttgactcc ggataatcgt tatgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aaaaacgagc tggatttcga aggagcttac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcaaagc aaaaatactc atcttttatt aaagaagttc aaaaggggaa cgatccgtta    840

accgcagcga agtcgatcgg gacggcctct ggttctaact tagaaaaact gcctaataac    900

ttgtattctg tacgtttgtc ccaaaaggac cgcgtgacct ttaatctgaa taatactgac    960

agtaccatga cgatccattc tgtaggcact cactacaaaa atatctaa               1008
```

<210> SEQ ID NO 69
<211> LENGTH: 1008
<212> TYPE: DNA
<213> ORGANISM: Artificial sequence
<220> FEATURE:
<223> OTHER INFORMATION: E. coli codon optimized coding sequence for
      Txp40_1 K119A/F169V/K213A mutant

<400> SEQUENCE: 69

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggagcttac    360

cctcagaata tctggaatat cccagacttg gaaaacaaac ctttgtcagc gtatagcgac    420
```

-continued

```
gacgataaac ttttggccct ttatttcttc gcagcacagg agattccgct ggaagagaat    480

caacaaagta atacagcccg ctttgttaag ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aagagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 70
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 K119/P134L/K213A mutant

<400> SEQUENCE: 70

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaagtt    240

atttatcagg agtatatgtc taatttgtcg tccgcactgc tgggagagaa cggcgatcag    300

atctctaaag acatggccga cggtttctac aagaacgagc tggatttcga aggagcttac    360

cctcagaata tctggaatat cccagacttg gaaaacaaac ttttgtcagc gtatagcgac    420

gacgataaac ttttggccct ttatttcttc gcagcacagg agattccgct ggaagagaat    480

caacaaagta atacagcccg ctttttttaag ttaattgact ttcttttttat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatctgaa taatactgac    960

agtaccatga cgatccattc tgtaggcact cactacaaaa atatctaa               1008
```

<210> SEQ ID NO 71
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 I101L/K103T/K119A/K213A/N257T mutant

<400> SEQUENCE: 71

```
atggtgattc agttgactcc ggataatcgt tctgggtatc cacccgttga gacgcagatc     60
```

```
gctggagaca ttgtgcgctt gttgaatttc aagcaaactg acgagggata cactgcaagt    120
catggaattg aatatcgtgc gaaaaagatc attttagctt atgcgttagc ggtttcagga    180
atccatgatg tatcccatct gcctggcgac tattacaaaa acaaggaaac ggcagaggtt    240
atttatcagg agtatatgtc taatttgtcg tccgcactgc tgggagagaa cggcgatcag    300
ctctctacag acatggccga cggtttctac aagaacgagc tggatttcga aggagcttac    360
cctcagaata tctggaatat cccagacttg gaaaacaaac ctttgtcagc gtatagcgac    420
gacgataaac ttttggccct ttatttcttc gcagcacagg agattccgct ggaagagaat    480
caacaaagta atacagcccg ctttttaag ttaattgact ttcttttcat tctttcggcc    540
gtgacttccc ttgggcgtcg tatttttagt aaaaattttt acaacgggct tgaatccaaa    600
tcgttagaga actacatcga acgcaagaaa ctttcggcac ctttcttccg cccaccccag    660
aaacttccgg acggtcgtat cgggtacctg gcttcgccca ccgaaccacc caagtggcgc    720
gttagtttac aggagctgaa aaataataaa tctcgcaacg gattcacgac catggagtcc    780
gctgcgaagc aaaaatactc atcgtttatt aaggaagttc aaaaggggaa cgatccgtta    840
accgcagcga agtcgatcgg gacggcctct ggttctaact tagaaaaact gcctaataac    900
ttgtattctg tacgcttgtc ccaaaaggac cgcgtgacct ttaatctgaa taatactgac    960
agtaccatga cgatccattc tgtaggcact cactacaaaa atatctaa                1008
```

<210> SEQ ID NO 72
<211> LENGTH: 1008
<212> TYPE: DNA
<213> ORGANISM: Artificial sequence
<220> FEATURE:
<223> OTHER INFORMATION: E. coli codon optimized coding sequence for
Txp40_1 H62Q/D99V/K119A/T165I/R167C/K213A mutant

<400> SEQUENCE: 72

```
atggtgattc agttgactcc ggataatcgt tctgggtatc cacccgttga gacgcagatc     60
gctggagaca ttgtgcgctt gttgaatttc aagcaaactg acgagggcta cactgcaagt    120
catggaattg aatatcgtgc gaaaaagatc attttagctt atgcgttagc ggtttcagga    180
atccaagatg tatcccatct gcctggcgac tattacaaga acaaggaaac ggcagaggtt    240
atttatcagg agtatatgtc taatttgtcg tccgcactgc tgggagagaa cggcgttcag    300
atctctaaag acatggccga cggtttctac aagaacgagc tggatttcga aggagcttac    360
cctcagaata tctggaatat cccagacttg gaaaacaaac ctttgtcagc gtatagcgac    420
gacgataaac ttttggccct ttatttcttc gcagcacagg agattccgct ggaagagaat    480
caacaaagta atatagcctg ctttttaag ttaattgact ttcttttcat tctttcggcc    540
gtgacttccc ttgggcgtcg tatttttagt aaaaattttt acaacgggct tgaatccaaa    600
tcgttagaga actacataga acgcaagaaa ctttcggctc ctttcttccg cccaccccag    660
aaacttccgg acggtcgtat cgggtacctg gcttcgccca ccgaaccacc caagtggcgc    720
gttagtttac aggagctgaa aaataataaa tctcgcaacg gattcacgaa catggagtcc    780
gctgcgaagc aaaaatactc atcgtttatt aaagaagttc aaaaggggaa cgatccgtta    840
accgcagcga agtcgatcgg gacggcctct ggttctaact tagaaaaact gcctaataac    900
ttgtattctg tacgcttgtc ccaaaaggac cgcgtgacct ttaatctgaa taatactgac    960
agtaccatga cgatccattc tgtaggcact cactacaaaa atatctaa                1008
```

<210> SEQ ID NO 73

-continued

<211> LENGTH: 1008
<212> TYPE: DNA
<213> ORGANISM: Artificial sequence
<220> FEATURE:
<223> OTHER INFORMATION: E. coli codon optimized coding sequence for Txp40_1 K119A/K213A/L316V mutant

<400> SEQUENCE: 73

```
atggtgattc agttgactcc ggataatcgt tctgggtatc cacccgttga gacgcagatc     60

gctggagaca ttgtgcgctt gttgaatttc aagcaaactg acgagggcta cactgcaagt    120

catggaattg aatatcgtgc gaaaaagatc attttagctt atgcgttagc ggtttcagga    180

atccatgatg tatcccatct gcctggcgac tattacaaga acaaggaaac ggcagaggtt    240

atttatcagg agtatatgtc taatttgtcg tccgcactgc tgggagagaa cggcgatcag    300

atctctaaag acatggccga cggtttctac aagaacgagc tggatttcga aggagcttac    360

cctcagaata tctggaatat cccagacttg gaaaacaaac ctttgtcagc gtatagcgac    420

gacgataaac ttttggccct ttatttcttc gcagcacagg agattccgct ggaagagaat    480

caacaaagta atacagcccg cttttttaaa ttaattgact ttcttttcat tctttcggcc    540

gtgacttccc ttgggcgtcg tatttttagt aaaaattttt acaacgggct tgaatccaaa    600

tcgttagaga actacatcga acgcaagaaa ctttcggctc ctttcttccg cccaccccag    660

aaacttccgg acggtcgtat cgggtacctg gcttcgccca ccgaaccacc caagtggcgc    720

gttagtttac aggagctgaa aaataataaa tctcgcaacg gattcacgaa catggagtcc    780

gctgcgaagc aaaaatactc atcgtttatt aaagaagttc aaaaggggaa cgatccgtta    840

accgcagcga agtcgatcgg gacggcctct ggttctaact tagaaaaact gcctaataac    900

ttgtattctg tacgcttgtc ccaaaaggac cgcgtgacct ttaatgtgaa taatactgac    960

agtaccatga cgatccattc tgtaggcact cactacaaaa atatctaa                1008
```

<210> SEQ ID NO 74
<211> LENGTH: 335
<212> TYPE: PRT
<213> ORGANISM: Artificial sequence
<220> FEATURE:
<223> OTHER INFORMATION: K31A mutant protein sequence

<400> SEQUENCE: 74

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140
```

```
Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 75
<211> LENGTH: 335
<212> TYPE: PRT
<213> ORGANISM: Artificial sequence
<220> FEATURE:
<223> OTHER INFORMATION: K48A mutant protein sequence

<400> SEQUENCE: 75

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Ala
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175
```

```
Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 76
<211> LENGTH: 335
<212> TYPE: PRT
<213> ORGANISM: Artificial Sequence
<220> FEATURE:
<223> OTHER INFORMATION: K49A mutant protein sequence

<400> SEQUENCE: 76

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205
```

-continued

Lys Lys Leu Ser Lys Pro Phe Phe Arg Pro Pro Gln Lys Leu Pro Asp
210 215 220

Gly Arg Ile Gly Tyr Leu Ala Ser Pro Thr Glu Pro Pro Lys Trp Arg
225 230 235 240

Val Ser Leu Gln Glu Leu Lys Asn Asn Lys Ser Arg Asn Gly Phe Thr
245 250 255

Asn Met Glu Ser Ala Ala Lys Gln Lys Tyr Ser Ser Phe Ile Lys Glu
260 265 270

Val Gln Lys Gly Asn Asp Pro Leu Thr Ala Ala Lys Ser Ile Gly Thr
275 280 285

Ala Ser Gly Ser Asn Leu Glu Lys Leu Pro Asn Asn Leu Tyr Ser Val
290 295 300

Arg Leu Ser Gln Lys Asp Arg Val Thr Phe Asn Leu Asn Asn Thr Asp
305 310 315 320

Ser Thr Met Thr Ile His Ser Val Gly Thr His Tyr Lys Asn Ile
325 330 335

<210> SEQ ID NO 77
<211> LENGTH: 335
<212> TYPE: PRT
<213> ORGANISM: Artificial sequence
<220> FEATURE:
<223> OTHER INFORMATION: K73A mutant protein sequence

<400> SEQUENCE: 77

Met Val Ile Gln Leu Thr Pro Asp Asn Arg Ser Gly Tyr Pro Pro Val
1 5 10 15

Glu Thr Gln Ile Ala Gly Asp Ile Val Arg Leu Leu Asn Phe Lys Gln
20 25 30

Thr Asp Glu Gly Tyr Thr Ala Ser His Gly Ile Glu Tyr Arg Ala Lys
35 40 45

Lys Ile Ile Leu Ala Tyr Ala Leu Ala Val Ser Gly Ile His Asp Val
50 55 60

Ser His Leu Pro Gly Asp Tyr Tyr Ala Asn Lys Glu Thr Ala Glu Val
65 70 75 80

Ile Tyr Gln Glu Tyr Met Ser Asn Leu Ser Ser Ala Leu Leu Gly Glu
85 90 95

Asn Gly Asp Gln Ile Ser Lys Asp Met Ala Asp Gly Phe Tyr Lys Asn
100 105 110

Glu Leu Asp Phe Glu Gly Lys Tyr Pro Gln Asn Ile Trp Asn Ile Pro
115 120 125

Asp Leu Glu Asn Lys Pro Leu Ser Ala Tyr Ser Asp Asp Asp Lys Leu
130 135 140

Leu Ala Leu Tyr Phe Phe Ala Ala Gln Glu Ile Pro Leu Glu Glu Asn
145 150 155 160

Gln Gln Ser Asn Thr Ala Arg Phe Phe Lys Leu Ile Asp Phe Leu Phe
165 170 175

Ile Leu Ser Ala Val Thr Ser Leu Gly Arg Arg Ile Phe Ser Lys Asn
180 185 190

Phe Tyr Asn Gly Leu Glu Ser Lys Ser Leu Glu Asn Tyr Ile Glu Arg
195 200 205

Lys Lys Leu Ser Lys Pro Phe Phe Arg Pro Pro Gln Lys Leu Pro Asp
210 215 220

Gly Arg Ile Gly Tyr Leu Ala Ser Pro Thr Glu Pro Pro Lys Trp Arg
225 230 235 240

```
Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 78
<211> LENGTH: 335
<212> TYPE: PRT
<213> ORGANISM: Artificial sequence
<220> FEATURE:
<223> OTHER INFORMATION: K75A mutant protein sequence

<400> SEQUENCE: 78

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Ala Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270
```

```
Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 79
<211> LENGTH: 335
<212> TYPE: PRT
<213> ORGANISM: Artificial sequence
<220> FEATURE:
<223> OTHER INFORMATION: K103A mutant protein sequence

<400> SEQUENCE: 79

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Ala Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300
```

```
Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 80
<211> LENGTH: 335
<212> TYPE: PRT
<213> ORGANISM: Artificial sequence
<220> FEATURE:
<223> OTHER INFORMATION: K111A mutant protein sequence

<400> SEQUENCE: 80

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Ala Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 81
<211> LENGTH: 335
<212> TYPE: PRT
<213> ORGANISM: Artificial sequence
<220> FEATURE:
<223> OTHER INFORMATION: K119A mutant protein sequence

<400> SEQUENCE: 81

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 82
<211> LENGTH: 335
<212> TYPE: PRT
<213> ORGANISM: Artificial sequence

```
<220> FEATURE:
<223> OTHER INFORMATION: K133A mutant protein sequence

<400> SEQUENCE: 82

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Ala Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 83
<211> LENGTH: 335
<212> TYPE: PRT
<213> ORGANISM: Artificial sequence
<220> FEATURE:
<223> OTHER INFORMATION: K143A mutant protein sequence

<400> SEQUENCE: 83

Met Val Ile Gln Leu Thr Pro Asp Asn Arg Ser Gly Tyr Pro Pro Val
```

```
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Ala Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 84
<211> LENGTH: 335
<212> TYPE: PRT
<213> ORGANISM: Artificial sequence
<220> FEATURE:
<223> OTHER INFORMATION: K170A mutant protein sequence

<400> SEQUENCE: 84

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
```

```
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Ala Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 85
<211> LENGTH: 335
<212> TYPE: PRT
<213> ORGANISM: Artificial sequence
<220> FEATURE:
<223> OTHER INFORMATION: K191A mutant protein sequence

<400> SEQUENCE: 85

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
```

```
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Ala Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 86
<211> LENGTH: 335
<212> TYPE: PRT
<213> ORGANISM: Artificial sequence
<220> FEATURE:
<223> OTHER INFORMATION: K200A mutant protein sequence

<400> SEQUENCE: 86

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
```

```
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Ala Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 87
<211> LENGTH: 335
<212> TYPE: PRT
<213> ORGANISM: Artificial sequence
<220> FEATURE:
<223> OTHER INFORMATION: K209A mutant protein sequence

<400> SEQUENCE: 87

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
```

```
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Ala Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 88
<211> LENGTH: 335
<212> TYPE: PRT
<213> ORGANISM: Artificial sequence
<220> FEATURE:
<223> OTHER INFORMATION: K210A mutant protein sequence

<400> SEQUENCE: 88

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
```

```
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Ala Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 89
<211> LENGTH: 335
<212> TYPE: PRT
<213> ORGANISM: Artificial sequence
<220> FEATURE:
<223> OTHER INFORMATION: K213A mutant protein sequence

<400> SEQUENCE: 89

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
```

```
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 90
<211> LENGTH: 335
<212> TYPE: PRT
<213> ORGANISM: Artificial sequence
<220> FEATURE:
<223> OTHER INFORMATION: K221A mutant protein sequence

<400> SEQUENCE: 90

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Ala Leu Pro Asp
    210                 215                 220

Gly Arg Ile Gly Tyr Leu Ala Ser Pro Thr Glu Pro Pro Lys Trp Arg
```

```
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 91
<211> LENGTH: 335
<212> TYPE: PRT
<213> ORGANISM: Artificial sequence
<220> FEATURE:
<223> OTHER INFORMATION: K238A mutant protein sequence

<400> SEQUENCE: 91

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Ala Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
```

-continued

```
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 92
<211> LENGTH: 335
<212> TYPE: PRT
<213> ORGANISM: Artificial sequence
<220> FEATURE:
<223> OTHER INFORMATION: K247A mutant protein sequence

<400> SEQUENCE: 92

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Ala Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
```

-continued

```
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 93
<211> LENGTH: 335
<212> TYPE: PRT
<213> ORGANISM: Artificial sequence
<220> FEATURE:
<223> OTHER INFORMATION: K250A mutant protein sequence

<400> SEQUENCE: 93

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Ala Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
```

325 330 335

<210> SEQ ID NO 94
<211> LENGTH: 335
<212> TYPE: PRT
<213> ORGANISM: Artificial sequence
<220> FEATURE:
<223> OTHER INFORMATION: K263A mutant protein sequence

<400> SEQUENCE: 94

Met Val Ile Gln Leu Thr Pro Asp Asn Arg Ser Gly Tyr Pro Pro Val
1 5 10 15

Glu Thr Gln Ile Ala Gly Asp Ile Val Arg Leu Leu Asn Phe Lys Gln
20 25 30

Thr Asp Glu Gly Tyr Thr Ala Ser His Gly Ile Glu Tyr Arg Ala Lys
35 40 45

Lys Ile Ile Leu Ala Tyr Ala Leu Ala Val Ser Gly Ile His Asp Val
50 55 60

Ser His Leu Pro Gly Asp Tyr Tyr Lys Asn Lys Glu Thr Ala Glu Val
65 70 75 80

Ile Tyr Gln Glu Tyr Met Ser Asn Leu Ser Ser Ala Leu Leu Gly Glu
85 90 95

Asn Gly Asp Gln Ile Ser Lys Asp Met Ala Asp Gly Phe Tyr Lys Asn
100 105 110

Glu Leu Asp Phe Glu Gly Lys Tyr Pro Gln Asn Ile Trp Asn Ile Pro
115 120 125

Asp Leu Glu Asn Lys Pro Leu Ser Ala Tyr Ser Asp Asp Asp Lys Leu
130 135 140

Leu Ala Leu Tyr Phe Phe Ala Ala Gln Glu Ile Pro Leu Glu Glu Asn
145 150 155 160

Gln Gln Ser Asn Thr Ala Arg Phe Phe Lys Leu Ile Asp Phe Leu Phe
165 170 175

Ile Leu Ser Ala Val Thr Ser Leu Gly Arg Arg Ile Phe Ser Lys Asn
180 185 190

Phe Tyr Asn Gly Leu Glu Ser Lys Ser Leu Glu Asn Tyr Ile Glu Arg
195 200 205

Lys Lys Leu Ser Lys Pro Phe Phe Arg Pro Pro Gln Lys Leu Pro Asp
210 215 220

Gly Arg Ile Gly Tyr Leu Ala Ser Pro Thr Glu Pro Pro Lys Trp Arg
225 230 235 240

Val Ser Leu Gln Glu Leu Lys Asn Asn Lys Ser Arg Asn Gly Phe Thr
245 250 255

Asn Met Glu Ser Ala Ala Ala Gln Lys Tyr Ser Ser Phe Ile Lys Glu
260 265 270

Val Gln Lys Gly Asn Asp Pro Leu Thr Ala Ala Lys Ser Ile Gly Thr
275 280 285

Ala Ser Gly Ser Asn Leu Glu Lys Leu Pro Asn Asn Leu Tyr Ser Val
290 295 300

Arg Leu Ser Gln Lys Asp Arg Val Thr Phe Asn Leu Asn Asn Thr Asp
305 310 315 320

Ser Thr Met Thr Ile His Ser Val Gly Thr His Tyr Lys Asn Ile
325 330 335

<210> SEQ ID NO 95
<211> LENGTH: 335
<212> TYPE: PRT

<213> ORGANISM: Artificial sequence
<220> FEATURE:
<223> OTHER INFORMATION: K265A mutant protein sequence

<400> SEQUENCE: 95

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Ala Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 96
<211> LENGTH: 335
<212> TYPE: PRT
<213> ORGANISM: Artificial sequence
<220> FEATURE:
<223> OTHER INFORMATION: K271A mutant protein sequence

<400> SEQUENCE: 96

-continued

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Ala Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 97
<211> LENGTH: 335
<212> TYPE: PRT
<213> ORGANISM: Artificial sequence
<220> FEATURE:
<223> OTHER INFORMATION: K275A mutant protein sequence

<400> SEQUENCE: 97

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30
```

```
Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Ala Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 98
<211> LENGTH: 335
<212> TYPE: PRT
<213> ORGANISM: Artificial sequence
<220> FEATURE:
<223> OTHER INFORMATION: K284A mutant protein sequence

<400> SEQUENCE: 98

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60
```

-continued

```
Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Ala Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 99
<211> LENGTH: 335
<212> TYPE: PRT
<213> ORGANISM: Artificial sequence
<220> FEATURE:
<223> OTHER INFORMATION: K296A mutant protein sequence

<400> SEQUENCE: 99

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95
```

```
Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Ala Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 100
<211> LENGTH: 335
<212> TYPE: PRT
<213> ORGANISM: Artificial sequence
<220> FEATURE:
<223> OTHER INFORMATION: K309A mutant protein sequence

<400> SEQUENCE: 100

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125
```

-continued

```
Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Ala Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 101
<211> LENGTH: 335
<212> TYPE: PRT
<213> ORGANISM: Artificial sequence
<220> FEATURE:
<223> OTHER INFORMATION: K333A mutant protein sequence

<400> SEQUENCE: 101

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160
```

```
Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Ala Asn Ile
                325                 330                 335
```

<210> SEQ ID NO 102
<211> LENGTH: 335
<212> TYPE: PRT
<213> ORGANISM: Artificial sequence
<220> FEATURE:
<223> OTHER INFORMATION: R10A mutant protein sequence

<400> SEQUENCE: 102

```
Met Val Ile Gln Leu Thr Pro Asp Asn Ala Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190
```

```
Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 103
<211> LENGTH: 335
<212> TYPE: PRT
<213> ORGANISM: Artificial sequence
<220> FEATURE:
<223> OTHER INFORMATION: R26A mutant protein sequence

<400> SEQUENCE: 103

Met Val Ile Gln Leu Thr Pro Asp Asn Arg Ser Gly Tyr Pro Pro Val
1               5                   10                  15

Glu Thr Gln Ile Ala Gly Asp Ile Val Ala Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220
```

```
Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 104
<211> LENGTH: 335
<212> TYPE: PRT
<213> ORGANISM: Artificial sequence
<220> FEATURE:
<223> OTHER INFORMATION: R46A mutant protein sequence

<400> SEQUENCE: 104

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Ala Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255
```

-continued

```
Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 105
<211> LENGTH: 335
<212> TYPE: PRT
<213> ORGANISM: Artificial sequence
<220> FEATURE:
<223> OTHER INFORMATION: R167A mutant protein sequence

<400> SEQUENCE: 105

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Ala Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285
```

```
Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 106
<211> LENGTH: 335
<212> TYPE: PRT
<213> ORGANISM: Artificial sequence
<220> FEATURE:
<223> OTHER INFORMATION: R186A mutant protein sequence

<400> SEQUENCE: 106

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Ala Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320
```

```
Ser Thr Met Thr Ile His Ser Val Gly Thr His Tyr Lys Asn Ile
                325                 330                 335


<210> SEQ ID NO 107
<211> LENGTH: 335
<212> TYPE: PRT
<213> ORGANISM: Artificial sequence
<220> FEATURE:
<223> OTHER INFORMATION: R187A mutant protein sequence

<400> SEQUENCE: 107

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Ala Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 108
<211> LENGTH: 335
```

-continued

```
<212> TYPE: PRT
<213> ORGANISM: Artificial sequence
<220> FEATURE:
<223> OTHER INFORMATION: R208A mutant protein sequence

<400> SEQUENCE: 108

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Ala
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 109
<211> LENGTH: 335
<212> TYPE: PRT
<213> ORGANISM: Artificial sequence
<220> FEATURE:
<223> OTHER INFORMATION: R217A mutant protein sequence

<400> SEQUENCE: 109
```

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Ala Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 110
<211> LENGTH: 335
<212> TYPE: PRT
<213> ORGANISM: Artificial Sequence
<220> FEATURE:
<223> OTHER INFORMATION: R226A mutant protein sequence

<400> SEQUENCE: 110

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30
```

```
Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Ala Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 111
<211> LENGTH: 335
<212> TYPE: PRT
<213> ORGANISM: Artificial sequence
<220> FEATURE:
<223> OTHER INFORMATION: R240A mutant protein sequence

<400> SEQUENCE: 111

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60
```

```
Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Ala
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 112
<211> LENGTH: 335
<212> TYPE: PRT
<213> ORGANISM: Artificial Sequence
<220> FEATURE:
<223> OTHER INFORMATION: R252A mutant protein sequence

<400> SEQUENCE: 112

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95
```

```
Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Ala Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 113
<211> LENGTH: 335
<212> TYPE: PRT
<213> ORGANISM: Artificial sequence
<220> FEATURE:
<223> OTHER INFORMATION: R305A mutant protein sequence

<400> SEQUENCE: 113

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125
```

```
Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Ala Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 114
<211> LENGTH: 335
<212> TYPE: PRT
<213> ORGANISM: Artificial sequence
<220> FEATURE:
<223> OTHER INFORMATION: R311A mutant protein sequence

<400> SEQUENCE: 114

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160
```

```
Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Ala Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 115
<211> LENGTH: 335
<212> TYPE: PRT
<213> ORGANISM: Artificial sequence
<220> FEATURE:
<223> OTHER INFORMATION: K31A/K49A double mutant protein sequence

<400> SEQUENCE: 115

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190
```

```
Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 116
<211> LENGTH: 335
<212> TYPE: PRT
<213> ORGANISM: Artificial sequence
<220> FEATURE:
<223> OTHER INFORMATION: K31A/K333A double mutant protein sequence

<400> SEQUENCE: 116

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220
```

```
Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Ala Asn Ile
                325                 330                 335
```

<210> SEQ ID NO 117
<211> LENGTH: 335
<212> TYPE: PRT
<213> ORGANISM: Artificial sequence
<220> FEATURE:
<223> OTHER INFORMATION: K31A/R208A double mutant protein sequence

<400> SEQUENCE: 117

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Ala
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255
```

```
Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 118
<211> LENGTH: 335
<212> TYPE: PRT
<213> ORGANISM: Artificial sequence
<220> FEATURE:
<223> OTHER INFORMATION: R208A/K333A double mutant protein sequence

<400> SEQUENCE: 118

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Ala
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285
```

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Ala Asn Ile
                325                 330                 335

<210> SEQ ID NO 119
<211> LENGTH: 335
<212> TYPE: PRT
<213> ORGANISM: Artificial sequence
<220> FEATURE:
<223> OTHER INFORMATION: K49A/R208A double mutant protein sequence

<400> SEQUENCE: 119

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Ala
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

```
Ser Thr Met Thr Ile His Ser Val Gly Thr His Tyr Lys Asn Ile
                325                 330                 335
```

<210> SEQ ID NO 120
<211> LENGTH: 335
<212> TYPE: PRT
<213> ORGANISM: Artificial sequence
<220> FEATURE:
<223> OTHER INFORMATION: K49A/K333A double mutant protein sequence

<400> SEQUENCE: 120

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Ala Asn Ile
                325                 330                 335
```

<210> SEQ ID NO 121

<211> LENGTH: 335
<212> TYPE: PRT
<213> ORGANISM: Artificial sequence
<220> FEATURE:
<223> OTHER INFORMATION: K31A/K49A/K333A mutant protein sequence

<400> SEQUENCE: 121

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Ala Asn Ile
                325                 330                 335
```

<210> SEQ ID NO 122
<211> LENGTH: 335
<212> TYPE: PRT
<213> ORGANISM: Artificial sequence
<220> FEATURE:
<223> OTHER INFORMATION: K31A/K49A/R208A/K333A mutant protein sequence

<400> SEQUENCE: 122

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Ala
        195                 200                 205

Lys Lys Leu Ser Lys Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Ala Asn Ile
                325                 330                 335
```

<210> SEQ ID NO 123
<211> LENGTH: 335
<212> TYPE: PRT
<213> ORGANISM: Artificial sequence
<220> FEATURE:
<223> OTHER INFORMATION: K73A/K213A double mutant protein sequence

<400> SEQUENCE: 123

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
```

```
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Ala Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 124
<211> LENGTH: 335
<212> TYPE: PRT
<213> ORGANISM: Artificial sequence
<220> FEATURE:
<223> OTHER INFORMATION: K103A/K213A double mutant protein sequence

<400> SEQUENCE: 124

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
```

```
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Ala Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 125
<211> LENGTH: 335
<212> TYPE: PRT
<213> ORGANISM: Artificial sequence
<220> FEATURE:
<223> OTHER INFORMATION: K213A/K284A double mutant protein sequence

<400> SEQUENCE: 125

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
```

```
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Ala Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 126
<211> LENGTH: 335
<212> TYPE: PRT
<213> ORGANISM: Artificial Sequence
<220> FEATURE:
<223> OTHER INFORMATION: K31A/K49A/K213A mutant protein sequence

<400> SEQUENCE: 126

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Ala Gln
            20                  25                  30

Thr Asp Glu Gly Tyr Thr Ala Ser His Gly Ile Glu Tyr Arg Ala Lys
        35                  40                  45

Ala Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
```

```
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 127
<211> LENGTH: 335
<212> TYPE: PRT
<213> ORGANISM: Artificial sequence
<220> FEATURE:
<223> OTHER INFORMATION: K119A/K213A double mutant protein sequence

<400> SEQUENCE: 127

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
```

-continued

```
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 128
<211> LENGTH: 335
<212> TYPE: PRT
<213> ORGANISM: Artificial sequence
<220> FEATURE:
<223> OTHER INFORMATION: K213A/R167A double mutant protein sequence

<400> SEQUENCE: 128

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Lys Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Ala Phe Phe Lys Leu Ile Asp Phe Leu Phe
                165                 170                 175

Ile Leu Ser Ala Val Thr Ser Leu Gly Arg Arg Ile Phe Ser Lys Asn
```

```
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 129
<211> LENGTH: 335
<212> TYPE: PRT
<213> ORGANISM: Artificial sequence
<220> FEATURE:
<223> OTHER INFORMATION: K119A/R167A double mutant protein sequence

<400> SEQUENCE: 129

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Ala Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Lys Pro Phe Phe Arg Pro Pro Gln Lys Leu Pro Asp
```

```
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 130
<211> LENGTH: 335
<212> TYPE: PRT
<213> ORGANISM: Artificial sequence
<220> FEATURE:
<223> OTHER INFORMATION: S11Y/M86I/K119A/K213T mutant protein sequence

<400> SEQUENCE: 130

Met Val Ile Gln Leu Thr Pro Asp Asn Arg Tyr Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Ile Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Thr Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
```

```
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 131
<211> LENGTH: 335
<212> TYPE: PRT
<213> ORGANISM: Artificial sequence
<220> FEATURE:
<223> OTHER INFORMATION: S11Y/K119A/K213A mutant protein sequence

<400> SEQUENCE: 131

Met Val Ile Gln Leu Thr Pro Asp Asn Arg Tyr Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
```

```
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335


<210> SEQ ID NO 132
<211> LENGTH: 335
<212> TYPE: PRT
<213> ORGANISM: Artificial sequence
<220> FEATURE:
<223> OTHER INFORMATION: K119A/F169V/K213A mutant protein sequence

<400> SEQUENCE: 132

Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Val Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
```

```
305                 310                 315                 320

Ser Thr Met Thr Ile His Ser Val Gly Thr His Tyr Lys Asn Ile
                325                 330                 335
```

<210> SEQ ID NO 133
<211> LENGTH: 335
<212> TYPE: PRT
<213> ORGANISM: Artificial sequence
<220> FEATURE:
<223> OTHER INFORMATION: K119A/P134L/K213A mutant protein sequence

<400> SEQUENCE: 133

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Leu Leu Ser Ala Tyr Ser Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 134
<211> LENGTH: 335
<212> TYPE: PRT
<213> ORGANISM: Artificial sequence
<220> FEATURE:
<223> OTHER INFORMATION: I101L/K103T/K119A/K213A/N257T mutant protein sequence

<400> SEQUENCE: 134

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Leu Ser Thr Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Thr Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 135
<211> LENGTH: 335
<212> TYPE: PRT
<213> ORGANISM: Artificial Sequence
<220> FEATURE:

<223> OTHER INFORMATION: H62Q/D99V/K119A/T165I/R167C/K213A mutant protein sequence

<400> SEQUENCE: 135

```
Met Val Ile Gln Leu Thr Pro Asp Asn Arg Ser Gly Tyr Pro Pro Val
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile Gln Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Val Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Ile Ala Cys Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Leu Asn Asn Thr Asp
305                 310                 315                 320

Ser Thr Met Thr Ile His Ser Val Gly Thr His Tyr Lys Asn Ile
                325                 330                 335
```

<210> SEQ ID NO 136
<211> LENGTH: 335
<212> TYPE: PRT
<213> ORGANISM: Artificial sequence
<220> FEATURE:
<223> OTHER INFORMATION: K119A/K213A/L316V mutant protein sequence

<400> SEQUENCE: 136

```
Met Val Ile Gln Leu Thr Pro Asp Asn Arg Ser Gly Tyr Pro Pro Val
```

-continued

```
1               5                   10                  15

Glu Thr Gln Ile Ala Gly Asp Ile Val Arg Leu Leu Asn Phe Lys Gln
            20                  25                  30

Thr Asp Glu Gly Tyr Thr Ala Ser His Gly Ile Glu Tyr Arg Ala Lys
        35                  40                  45

Lys Ile Ile Leu Ala Tyr Ala Leu Ala Val Ser Gly Ile His Asp Val
    50                  55                  60

Ser His Leu Pro Gly Asp Tyr Tyr Lys Asn Lys Glu Thr Ala Glu Val
65                  70                  75                  80

Ile Tyr Gln Glu Tyr Met Ser Asn Leu Ser Ser Ala Leu Leu Gly Glu
                85                  90                  95

Asn Gly Asp Gln Ile Ser Lys Asp Met Ala Asp Gly Phe Tyr Lys Asn
            100                 105                 110

Glu Leu Asp Phe Glu Gly Ala Tyr Pro Gln Asn Ile Trp Asn Ile Pro
        115                 120                 125

Asp Leu Glu Asn Lys Pro Leu Ser Ala Tyr Ser Asp Asp Asp Lys Leu
    130                 135                 140

Leu Ala Leu Tyr Phe Phe Ala Ala Gln Glu Ile Pro Leu Glu Glu Asn
145                 150                 155                 160

Gln Gln Ser Asn Thr Ala Arg Phe Phe Lys Leu Ile Asp Phe Leu Phe
                165                 170                 175

Ile Leu Ser Ala Val Thr Ser Leu Gly Arg Arg Ile Phe Ser Lys Asn
            180                 185                 190

Phe Tyr Asn Gly Leu Glu Ser Lys Ser Leu Glu Asn Tyr Ile Glu Arg
        195                 200                 205

Lys Lys Leu Ser Ala Pro Phe Phe Arg Pro Pro Gln Lys Leu Pro Asp
    210                 215                 220

Gly Arg Ile Gly Tyr Leu Ala Ser Pro Thr Glu Pro Pro Lys Trp Arg
225                 230                 235                 240

Val Ser Leu Gln Glu Leu Lys Asn Asn Lys Ser Arg Asn Gly Phe Thr
                245                 250                 255

Asn Met Glu Ser Ala Ala Lys Gln Lys Tyr Ser Ser Phe Ile Lys Glu
            260                 265                 270

Val Gln Lys Gly Asn Asp Pro Leu Thr Ala Ala Lys Ser Ile Gly Thr
        275                 280                 285

Ala Ser Gly Ser Asn Leu Glu Lys Leu Pro Asn Asn Leu Tyr Ser Val
    290                 295                 300

Arg Leu Ser Gln Lys Asp Arg Val Thr Phe Asn Val Asn Asn Thr Asp
305                 310                 315                 320

Ser Thr Met Thr Ile His Ser Val Gly Thr His Tyr Lys Asn Ile
                325                 330                 335
```